United States Patent
Ittner et al.

(10) Patent No.: US 10,634,688 B2
(45) Date of Patent: Apr. 28, 2020

(54) ASSAY AND METHOD FOR IDENTIFYING COMPOUNDS THAT REDUCE SIL1 EXPRESSION OR ACTIVITY

(71) Applicant: Macquarie University, North Ryde, NSW (AU)

(72) Inventors: Lars Matthias Ittner, Chatswood (AU); Janet Van Eersel, Glebe (AU)

(73) Assignee: MACQUARIE UNIVERSITY, North Ryde (AU)

( * ) Notice: Subject to any disclaimer, the term of this patent is extended or adjusted under 35 U.S.C. 154(b) by 195 days.

(21) Appl. No.: 14/773,115

(22) PCT Filed: Mar. 6, 2014

(86) PCT No.: PCT/AU2014/000225
§ 371 (c)(1),
(2) Date: Sep. 4, 2015

(87) PCT Pub. No.: WO2014/134685
PCT Pub. Date: Sep. 12, 2014

(65) Prior Publication Data
US 2016/0018417 A1 Jan. 21, 2016

(30) Foreign Application Priority Data
Mar. 6, 2013 (AU) ................................ 2013900812

(51) Int. Cl.
*G01N 33/68* (2006.01)
*C12Q 1/6883* (2018.01)

(52) U.S. Cl.
CPC ....... *G01N 33/6896* (2013.01); *C12Q 1/6883* (2013.01); *C12Q 2600/136* (2013.01); *G01N 2333/4709* (2013.01); *G01N 2500/02* (2013.01)

(58) Field of Classification Search
CPC ............ C12Q 1/6883; C12Q 2600/136; G01N 33/6896; G01N 2500/02
See application file for complete search history.

(56) References Cited

FOREIGN PATENT DOCUMENTS

WO 2004096199 A2 11/2004
WO 2009133142 A1 11/2009

OTHER PUBLICATIONS

Liu et al. SIL1 Rescued Bip Elevation-Related Tau Hyperphosphorylation in ER Stress. Mol Neurobiol. Mar. 2016;53(2):983-94. doi: 10.1007/s12035-014-9039-4. Epub Jan. 10, 2015.*
Zimmermann, R. et al. "Protein transport into the endoplasmic reticulum: mechanisms and pathologies." Trends in Molecular Medicine, 2006, vol. 12, No. 12, pp. 567-573.
Zhao, L. et al. "Protein accumulation and neurodegeneration in the woozy mutant mouse is caused by disruption of SIL1, a cochaperone of BiP." Nature Genetics, 2005, vol. 37, No. 9, pp. 974-979.
Guzman-Martinez, L. et al. "Tau oligomer; as potential targets for Alzheimer's diagnosis and novel drugs." Frontiers in Neurology, Oct. 28, 2013,. vol. 4, article 167.
International Search Report and Written Opinion dated May 8, 2014 from PCT International Application No. PCT/AU2014/000225.
Hoozemans, J. J. M. & Scheper, W., Book Section: "Endoplasmic reticulum stress in neurodegeneration." In: Ovadi, J. & Orosz. F. (Eds). Protein Folding and Misfolding: Neurodegenerative Diseases, Focus on Structural Biology, 2009, vol. 7. pp. 111-132.
Altschul et al., "Basic Local Alignment Search Tool," J. Mol. Biol., 1990, 215:403-410.
Altschul et al., "Gapped BLAST and PSI-BLAST: a new generation of protein database search programs," Nucleic Acids Res., 1997, 25(17):3389-3402.
Brooks et al., "CHARMM: A Program for Macromolecular Energy, Minimization, and Dynamics Calculations," J Comp Chem., 1983, 4:187-217.
Bugg et al., "Drugs by Design," Scientific American, 1993, pp. 92-98.
Cwirla et al., "Peptides on phage: A vast library of peptides for identifying ligands," Proc Natl Acad Sci, 1990, 37:6378-6382.
Devlin et al., "Random Peptide Libraries: A Source of Specific Protein Binding Molecules," Science, 1990, 249:404-406.
Salameau et al., "β-Lactamase protein fragment complementation assays as in vivo and in vitro sensors of protein-protein interactions," Nat Biotechnol., 2002, 20:619-22.
Ghosh et al., "Antiparallel Leucine Zipper-Directed Protein Reassembly: Application to the Green Fluorescent Protein," J. Am. Chem. Soc., 2000, 122:5658-5659.
Thompson et al., "Clustal W: improving the sensitivity of progressive multiple sequence alignment through sequence weighting, position-specific gap penalties and weight matrix choice," Nucleic Acids Res., 1994, 22 r,22):4673-4680.
Hu et al., "Simultaneous visualization of multiple protein interactions in living cells using multicolor fluorescence complementation analysis," Nat Biotechnol, 2003, 21(5): 539-45.

(Continued)

*Primary Examiner* — Gregory S Emch
(74) *Attorney, Agent, or Firm* — Michael Best & Friedrich LLP

(57) ABSTRACT

The invention relates to methods and assays for identifying compounds as candidates in the development of a drug for the treatment of various diseases including those associated with pathological Tau. The invention also relates to methods and assays for identifying compounds for the treatment of various diseases including those associated with pathological Tau. The invention also relates to cell lines and constructs for use in an assay of the invention. The methods and assays identify a compound as useful in the treatment of a tauopathy if said compound modulates Sil1 expression or activity.

13 Claims, 11 Drawing Sheets
Specification includes a Sequence Listing.

(56) References Cited

OTHER PUBLICATIONS

Johnsson et al., "Split ubiquitin as a sensor of protein interactions in vivo," Proc Natl Acad Sci USA, 1994, 91:10340-4.
Jung et al., "Surface plasmon resonance imaging-based protein arrays for high-throughput screening of protein-protein interaction inhibitors," Proteomics, 2005, 5:4427-4431.
Karlin and Altschul, "Methods for assessing the statistical significance of molecular sequence features by using general scoring schemes," Proc. Natl. Acad. Sci., 1990, 87:2264-2268.
Karlin and Altschul, "Application and statistics for multiple high-scoring segments in molecular sequences," Proc. Natl. Acad. Sci., 1993, 90:5873-5877.
MacDonald et al., "Identifing off-target effects and hidden phenotypes of drugs in human cells," Nat Chem Biol, 2006, 2:329-337.
Meng et al., "Automated Docking with Grid-Based Energy Evaluation," J Comp Chem, 1992, 13:505-524.
Morris et al., "Automated Docking Using a Lamarckian Genetic Algorithm and an Empirical Binding Free Energy Function," J. Computational Chemistry, 1998, 19:1639-1662.
Myers and Miller, "Optimal alignments in linear space," CABIOS, 1988, 4(1):11-17.
Paulmurugan et al., "Noninvasive imaging of protein-protein interactions in living subjects by using reporter protein, implementation and reconstitution strategies," Proc Natl Acad Sci USA, 2002, 99:15608-13.
Pelletier et al.,"Oligomerization domain-directed reassembly of active dihydrofolate reductase from rationally designed fragments," Proc Natl Acad Sci USA, 1998, 95:12141-6.
Remy et al., "A highly sensitive protein-protein interaction assay based on Gaussia luciferase," Nat Methods, 2006, 3, 977-9.
Rossi et al., "Monitoring protein-protein interactions in intact eukaryotic cells by $\beta$-galactosidase complementation," Proc Natl Acad Sci USA, 1997, 94, 8405-10.
Scott et al., "Searching for Peptide Ligands with an Epitope Library," Science, 1990, 249:386-390.
West et al.,"Targeting HIV-1 protaese: a test of drug-design methodologies," TIPS, 1995, 16:67-74.
Zoghbi et al., "SILencing misbehaving proteins," Nature Genetics, 2005, 37(12):1302-1303.

\* cited by examiner

FIG. 4C
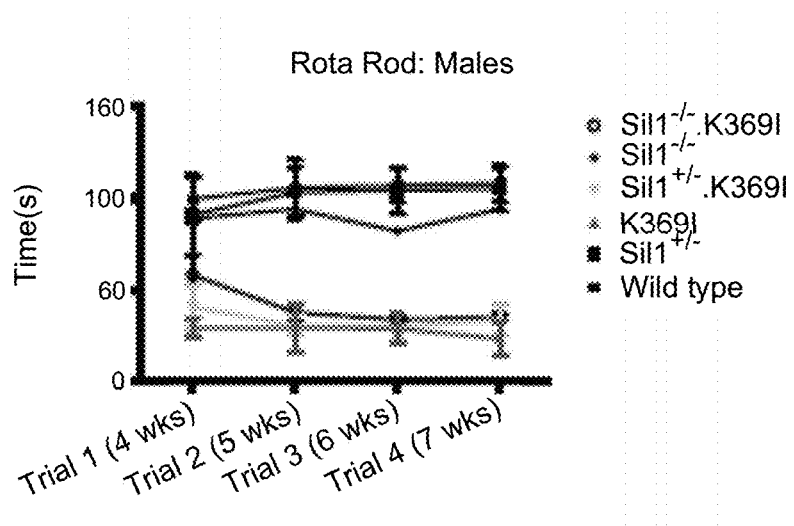
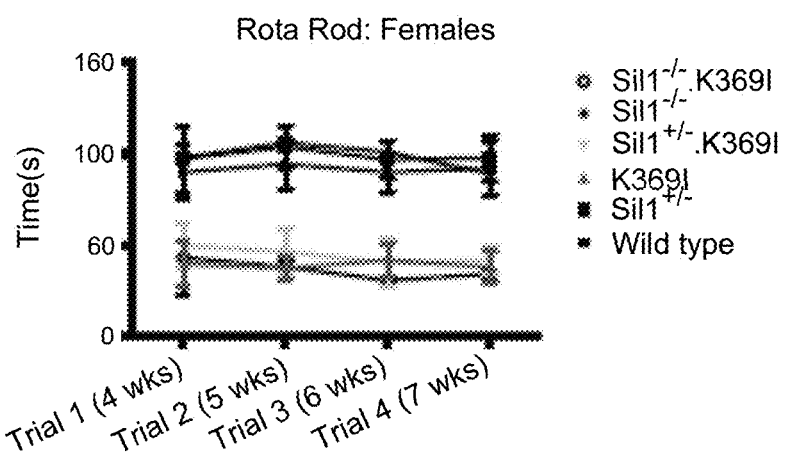
FIG. 4D
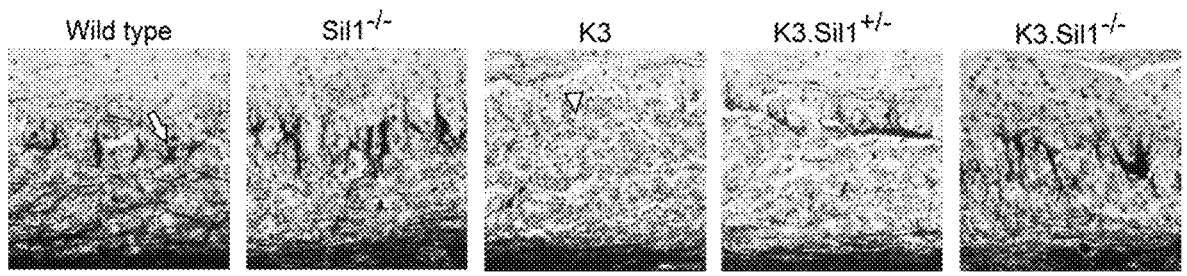

FIG. 5

SEQ ID NO: 1

<u>ATGGCTCCCCAGAGCCTGCCTTCATCTAGGATGGCTCCTCTGGGCATGCTGCTTGGGCTG</u>
<u>CTGATGGCCGCCTGCTTCACCTTCTGCCTC</u>AGTCATCAGAACCTGAAGGAGTTTGCCCTGACCA
ACCCAGAGAAGAGCAGCACCAAAGAAACAGAGAGAAAAGAAACCAAAGCCGAGGAGGAGCTGGA
TGCCGAAGTCCTGGAGGTGTTCCACCCGACGCATGAGTGGCAGGCCCTTCAGCCAGGGCAGGCT
GTCCCTGCAGGATCCCACGTACGGCTGAATCTTCAGACTGGGGAAAGAGAGGCAAAACTCCAAT
ATGAGGACAAGTTCCGAAATAATTTGAAAGGCAAAAGGCTGGATATCAACACCAACACCTACAC
ATCTCAGGATCTCAAGAGTGCACTGGCAAAATTCAAGGAGGGGCAGAGATGGAGAGTTCAAAG
GAAGACAAGGCAAGGCAGGCTGAGGTAAAGCGGCTCTTCCGCCCATTGAGGAACTGAAGAAAG
ACTTTGATGAGCTGAATGTTGTCATTGAGACTGACATGCAGATCATGGTACGGCTGATCAACAA
GTTCAATAGTTCCAGCTCCAGTTTGGAAGAGAAGATTGCTGCGCTCTTTGATCTTGAATATTAT
GTCCATCAGATGGACAATGCGCAGGACCTGCTTTCCTTTGGTGGTCTTCAAGTGGTGATCAATG
GGCTGAACAGCACAGAGCCCCTCGTGAAGGAGTATGCTGCGTTTGTGCTGGGCGCTGCCTTTTC
CAGCAACCCCAAGGTCCAGGTGGAGGCCATCGAAGGGGAGCCCTGCAGAAGCTGCTGGTCATC
CTGGCCACGGAGCAGCCGCTCACTGCAAAGAAGAAGGTCCTGTTTGCACTGTGCTCCCTGCTGC
GCCACTTCCCCTATGCCCAGCGGCAGTTCCTGAAGCTCGGGGGGCTGCAGGTCCTGAGGACCCT
GGTGCAGGAGAAGGGCACGGAGGTGCTCGCCGTGCGCGTGGTCACACTGCTCTACGACCTGGTC
ACGGAGAAGATGTTCGCCGAGGAGGAGGCTGAGCTGACCCAGGAGATGTCCCCAGAGAAGCTGC
AGCAGTATCGCCAGGTACACCTCCTGCCAGGCCTGTGGGAACAGGGCTGGTGCGAGATCACGGC
CCACCTCCTGGCGCTGCCCGAGCATGATGCCCGTGAGAAGGTGCTGCAGACACTGGGCGTCCTC
CTGACCACCTGCCGGGACCGCTACCGTCAGGACCCCAGCTCGGCAGGACACTGGCCAGCCTGC
AGGCTGAGTACCAGGTGCTGGCCAGCCTGGAGCTGCAGGATGGTGAGGACGAGGGCTACTTCCA
GGAGCTGCTGGGCTCTGTCAACAGCTTGCTG*AAGGAGCTGAGA*

FIG. 6

SEQ ID NO: 2

```
  1 mapqslpssr maplgmllgl lmaacftfcl shqnlkefal tnpeksstke terketkaee 61 eldaevlevf hpthewqalq pgqavpagsh vrlnlqtger eaklqyedkf rnnlkgkrld 121 intntytsqd lksalakfke gaemessked karqaevkrl frpieelkkd fdelnvviet 181 dmqimvrlin kfnsssssle ekiaalfdle yyvhqmdnaq dllsfgglqv vinglnstep 241 lvkeyaafvl gaafssnpkv qveaieggal qkllvilate qpltakkkvl falcsllrhf 301 pyaqrqflkl gglqvlrtlv qekgtevlav rvvtllydlv tekmfaeeea eltqemspek 361 lqqyrqvhll pglweqgwce itahllalpe hdarekvlqt lgvllttcrd ryrqdpqlgr 421 tlaslqaeyq vlaslelqdg edegyfqell gsvnsllkel r
```

FIG. 7

SEQ ID NO: 3

MKLSLVAAMLLLLSAARAEEEDKKEDVGTVVGIDLGTTYSCVGV

FKNGRVEIIANDQGNRITPSYVAFTPEGERLIGDAAKNQLTSNPENTVFDAKRLIGRT

WNDPSVQQDIKFLPFKVVEKKTKPYIQVDIGGGQTKTFAPEEISAMVLTKMKETAEAY

LGKKVTHAVVTVPAYFNDAQRQATKDAGTIAGLNVMRIINEPTAAAIAYGLDKREGEK

NILVFDLGGGTFDVSLLTIDNGVFEVVATNGDTHLGGEDFDQRVMEHFIKLYKKKTGK

DVRKDNRAVQKLRREVEKAKRALSSQHQARIEIESFYEGEDFSETLTRAKFEELNMDL

FRSTMKPVQKVLEDSDLKKSDIDEIVLVGGSTRIPKIQQLVKEFFNGKEPSRGINPDE

AVAYGAAVQAGVLSGDQDTGDLVLLDVCPLTLGIETVGGVMTKLIPRNTVVPTKKSQI

FSTASDNQPTVTIKVYEGERPLTKDNHLLGTFDLTGIPPAPRGVPQIEVTFEIDVNGI

LRVTAEDKGTGNKNKITITNDQNRLTPEEIERMVNDAEKFAEEDKKLKERIDTRNELE

SYAYSLKNQIGDKEKLGGKLSSEDKETMEKAVEEKIEWLESHQDADIEDFKAKKKELE

EIVQPIISKLYGSAGPPPTGEEDTAEKDEL

FIG. 8

SEQ ID NO: 4

```
  1 maeprqefev medhagtygl gdrkdqggyt mhqdqegdtd aglkesplqt ptedgseepg 61 setsdakstp taedvtaplv degapgkqaa aqphteipeg ttaeeagigd tpsledeaag 121 hvtqarmvsk skdgtgsddk kakgadgktk iatprgaapp gqkgqanatr ipaktppapk 181 tppsgeppk sgdrsgyssp gspgtpgsrs rtpslptppt repkkvavvr tppkspssak 241 srlqtapvpm pdlknvkski gstenlkhqp gggkvqiink kldlsnvqsk cgskdnikhv 301 pgggsvqivy kpvdlskvts kcgslgnihh kpgggqvevk sekldfkdrv qskigsldni 361 thvpgggnkk iethkltfre nakaktdhga eivykspvvs gdtsprhlsn vsstgsidmv 421 dspqlatlad evsaslakqg l
```

ASSAY AND METHOD FOR IDENTIFYING COMPOUNDS THAT REDUCE SIL1 EXPRESSION OR ACTIVITY

CROSS REFERENCE TO RELATED APPLICATIONS

This application is a 35 U.S.C. § 371 National Stage Entry of International Application No. PCT/AU2014/000225 having an international filing date of Mar. 6, 2014, which claims the benefit of Australia Provisional Application No. 2013900812, filed Mar. 6, 2013, the content of each of the aforementioned applications is incorporated herein by reference in its entirety.

FIELD OF THE INVENTION

The invention relates to methods and assays for identifying compounds as candidates in the development of a drug for the treatment of various diseases including those associated with pathological Tau. The invention also relates to methods and assays for identifying compounds for the treatment of various diseases including those associated with pathological Tau. The invention also relates to cell lines and constructs for use in an assay of the invention.

BACKGROUND OF THE INVENTION

In normal physiology the Tau protein promotes microtubule assembly and stability and is critical for the function of axons. However, Tau has been identified in a highly phosphorylated form as the filamentous core of the neurofibrillary tangles (NFT) or insoluble tau aggregates. Accumulation of NFTs or other inclusions containing Tau in the brain are histopathological features of many neurodegenerative diseases, which are collectively known as tauopathies. Tauopathies include, e.g., Alzheimer's disease (AD), Pick's disease (PiD), progressive supranuclear palsy (PSP), corticobasal degeneration (CBD), and frontotemporal lobar degeneration (FTLD).

It is predicted that about half of the estimated one billion people over the age of 65 in 2050 will have some Tau inclusions (e.g., neurofibrillary tangles (NFT)) in their brains.

The best-known tauopathy is Alzheimer's disease (AD), where the Tau protein is deposited within neurons in the form of neurofibrillary tangles (NFTs). Tangles are formed by hyperphosphorylation of Tau, causing it to aggregate in an insoluble form. These aggregations of hyperphosphorylated tau protein are also referred to as PHF, or "paired helical filaments".

There is a large and rapidly growing unmet need for disease modifying drugs for Alzheimer's disease (AD) and other tauopathies.

The molecular interactions that underlie the formation of neurofibrillary tangles (NFT) or insoluble tau aggregates are presently unknown.

There is a need for assays and related methods for identifying compounds that are likely to inhibit the pathological function of Tau, such as the formation of neurofibrillary tangles.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

SUMMARY OF THE INVENTION

The invention seeks to address at least one of the above identified needs.

The invention provides a method for determining whether a compound is useful in the treatment of a tauopathy including the steps of:
  providing a test compound;
  providing a system that allows Sil1 expression or activity to be measured;
  contacting the system with the compound in conditions for permitting the compound to modulate Sil1 expression or activity;
  determining whether Sil1 expression or activity is modulated;
wherein a modulation, typically a reduction, in Sil1 expression or activity indicates that the compound is useful in the treatment of a tauopathy. Typically the system is a cell line or animal model. Preferably, the method further comprises determining whether the compound reduces neurofibrillary tangles.

The invention provides a method for determining whether a compound is useful in the treatment of a tauopathy including the steps of:
  providing a test compound;
  providing a Sil1 protein, a Tau protein and a BiP protein, in conditions that allow the formation of a complex between Sil1, Tau and BiP proteins;
  contacting the complex with the compound in conditions for permitting the compound to bind to any of the Sil1 protein, the Tau protein or the BiP protein;
  determining whether a complex between Sil1, Tau and BiP is present;
wherein an absence of, or reduction in, the complex indicates that the compound is useful in the treatment of a tauopathy. Typically determining whether a complex between Sil1, Tau and BiP is present is by determining whether Sil1, Tau and/or BiP has dissociated from the complex.

The invention provides a method for determining whether a compound is useful in the treatment of a tauopathy including the steps of:
  providing a compound for which a capacity to reduce interaction between a Sil1 protein and a Tau protein is to be determined;
  providing a Sil1 protein and a Tau protein, wherein the Sil1 protein includes a domain for binding the Tau protein, and wherein the Sil1 and/or Tau proteins are adapted to form a detectable signal when the Sil1 protein is bound to the Tau protein;
  contacting the Sil1 protein and the Tau protein with the compound in conditions for permitting the compound to bind to either or both of the Sil1 protein and Tau protein, thereby inhibiting the binding of the Sil1 protein to the Tau protein when the compound is bound to either or both of Sil1 protein and Tau protein;
  determining whether a detectable signal is formed from binding of Sil1 protein to Tau protein;
wherein an absence of, or reduction in, a detectable signal indicates that the compound inhibits the binding of the Sil1 protein to the Tau protein,
thereby determining whether the compound is useful in the treatment of a tauopathy.

The present invention provides a method for determining whether a compound is useful in the treatment of a tauopathy including the steps of:
- providing a compound;
- providing a Sil1 protein and a Tau protein, wherein the Sil1 protein includes a domain for binding the Tau protein, and wherein the Sil1 and/or Tau proteins are adapted to form a detectable signal when the Sil1 protein is bound to the Tau protein;
- contacting the Sil1 protein and the Tau protein with the compound in conditions for permitting the compound to bind to either or both of the Sil1 protein and Tau protein, thereby inhibiting the binding of the Sil1 protein to the Tau protein when the compound is bound to either or both of Sil1 protein and Tau protein;
- determining whether a detectable signal is formed from binding of Sil1 protein to Tau protein;

wherein an absence of a detectable signal indicates that the compound is useful in the treatment of a tauopathy.

The present invention also provides a method for identifying a compound for the treatment of a tauopathy including the steps of
- providing the coordinates of a molecule of a Sil1 protein to a computerized modelling system;
- identifying a compound that is likely to bind to a Sil1 protein at a site on the Sil1 protein that is involved in the interaction with a Tau protein. Preferably, the method further comprises
- obtaining or synthesizing the compound identified; and
- contacting a Sil1 protein with the compound in conditions for permitting the compound to bind to the Sil1 protein to confirm whether the compound binds a Sil1 protein.

The present invention also provides a method for identifying a compound for the treatment of a tauopathy including the steps of:
- supplying a computer modelling application with a set of structure co-ordinates for a Sil1 protein, wherein the Sil1 protein comprises at least a portion of the region identified to interact with a Tau protein;
- supplying the computer modelling application with a set of structure coordinates for a test compound; and
- determining whether the test compound is expected to bind to the Sil1 protein on the region identified to interact with a Tau protein wherein binding of the test compound to the Sil1 protein on the region identified to interact with a Tau protein is indicative of the test compound being useful in the treatment of a tauopathy. Preferably, determining whether the test compound is expected to bind to the Sil1 protein includes performing a fitting operation between the test compound and the portion of the region of Sil1 identified to interact with a Tau protein, followed by computationally analysing the results of the fitting operation to quantify the association between the test compound and the Sil1 protein. Preferably, the computer modelling system is supplied with a set of structure coordinates for a library of test compounds.

The invention provides a method for determining whether a compound is useful in the treatment of a tauopathy including the steps of:
- providing a compound for which a capacity to reduce interaction between a Sil1 protein and a BiP protein is to be determined;
- providing a Sil1 protein and a BiP protein, wherein the Sil1 protein includes a domain for binding the BiP protein, and wherein the Sil1 and/or BiP proteins are adapted to form a detectable signal when the Sil1 protein is bound to the BiP protein;
- contacting the Sil1 protein and the BiP protein with the compound in conditions for permitting the compound to bind to either or both of the Sil1 protein and BiP protein, thereby inhibiting the binding of the Sil1 protein to the BiP protein when the compound is bound to either or both of Sil1 protein and BiP protein;
- determining whether a detectable signal is formed from binding of Sil1 protein to BiP protein;

wherein an absence of, or reduction in, a detectable signal indicates that the compound inhibits the binding of the Sil1 protein to the BiP protein, thereby determining whether the compound is useful in the treatment of a tauopathy.

The present invention also provides a method for identifying a compound for the treatment of a tauopathy including the steps of
- providing the coordinates of a molecule of a Sil1 protein to a computerized modelling system;
- identifying a compound that is likely to bind to a Sil1 protein at a site on the Sil1 protein that is involved in the interaction with a BiP protein. Preferably, the method further comprises
- obtaining or synthesizing the compound identified; and
- contacting a Sil1 protein with the compound in conditions for permitting the compound to bind to the Sil1 protein to confirm whether the compound binds a Sil1 protein.

The present invention also provides a method for identifying a compound for the treatment of a tauopathy including the steps of:
- supplying a computer modelling application with a set of structure co-ordinates for a Sil1 protein, wherein the Sil1 protein comprises at least a portion of the region identified to interact with a BiP protein;
- supplying the computer modelling application with a set of structure coordinates for a test compound; and
- determining whether the test compound is expected to bind to the Sil1 protein on the region identified to interact with a BiP protein wherein binding of the test compound to Sil1 protein on the region identified to interact with a BiP protein is indicative of the test compound being useful in the treatment of a tauopathy. Preferably, determining whether the test compound is expected to bind to the Sil1 protein includes performing a fitting operation between the test compound and the portion of the region of Sil1 identified to interact with a BiP protein, followed by computationally analysing the results of the fitting operation to quantify the association between the test compound and the Sil1 protein. Preferably, the computer modelling system is supplied with a set of structure coordinates for a library of test compounds.

The invention provides a method for determining whether a compound is useful in the treatment of a tauopathy including the steps of:
- providing a compound for which a capacity to reduce interaction between a Tau protein and a BiP protein is to be determined;
- providing a Tau protein and a BiP protein, wherein the Tau protein includes a domain for binding the BiP protein, and wherein the Tau and/or BiP proteins are adapted to form a detectable signal when the Tau protein is bound to the BiP protein;
- contacting the Tau protein and the BiP protein with the compound in conditions for permitting the compound to bind to either or both of the Tau protein and BiP protein, thereby inhibiting the binding of the Tau protein to the BiP protein when the compound is bound to either or both of Tau protein and BiP protein;

determining whether a detectable signal is formed from binding of Tau protein to BiP protein;

wherein an absence of a detectable signal indicates that the compound inhibits the binding of the Tau protein to the BiP protein, thereby determining whether the compound is useful in the treatment of a tauopathy.

The invention provides a method for determining whether a compound is useful in the treatment of a tauopathy including the steps of:

providing a compound;

providing a Tau protein and a BiP protein, wherein the Tau protein includes a domain for binding the BiP protein, and wherein the Tau and/or BiP proteins are adapted to form a detectable signal when the Tau protein is bound to the BiP protein;

contacting the Tau protein and the BiP protein with the compound in conditions for permitting the compound to bind to either or both of the Tau protein and BiP protein, thereby inhibiting the binding of the Tau protein to the BiP protein when the compound is bound to either or both of Tau protein and BiP protein;

determining whether a detectable signal is formed from binding of Tau protein to BiP protein;

wherein an absence of a detectable signal indicates that the compound is useful in the treatment of a tauopathy.

In another embodiment there is provided a nucleic acid encoding a Sil1 protein that is adapted to form a detectable signal when the Sil1 protein is bound to Tau protein.

In another embodiment there is provided a nucleic acid encoding a Tau protein that is adapted to form a detectable signal when the Tau protein is bound to Sil1 protein.

In another embodiment there is provided a nucleic acid encoding a Sil1 protein that is adapted to form a detectable signal when the Sil1 protein is bound to BiP protein.

In another embodiment there is provided a nucleic acid encoding a BiP protein that is adapted to form a detectable signal when the BiP protein is bound to Sil1 protein.

In another embodiment there is provided a nucleic acid encoding a Tau protein that is adapted to form a detectable signal when the Tau protein is bound to BiP protein.

In another embodiment there is provided a nucleic acid encoding a BiP protein that is adapted to form a detectable signal when the BiP protein is bound to Tau protein.

In another embodiment there is provided a vector or construct including a nucleic acid described above.

In another embodiment there is provided a cell including a nucleic acid, vector or construct described above.

The present invention also provides a method for identifying a compound for the treatment of a tauopathy including the steps of providing the coordinates of a molecule of a BiP protein to a computerized modelling system;

identifying a compound that is likely to bind to a BiP protein at a site on the BiP protein that is involved in the interaction with a Tau protein. Preferably, the method further comprises obtaining or synthesizing the compound identified; and contacting a BiP protein with the compound in conditions for permitting the compound to bind to the BiP protein to confirm whether the compound binds a BiP protein.

The present invention also provides a method for identifying a compound for the treatment of a tauopathy including the steps of:

supplying a computer modelling application with a set of structure co-ordinates for a BiP protein, wherein the BiP protein comprises at least a portion of the region identified to interact with a Tau protein;

supplying the computer modelling application with a set of structure coordinates for a test compound; and determining whether the test compound is expected to bind to the BiP protein on the region identified to interact with a Tau protein wherein binding of the test compound to BiP protein on the region identified to interact with a Tau protein is indicative of the test compound being useful in the treatment of a tauopathy. Preferably, determining whether the test compound is expected to bind to the BiP protein includes performing a fitting operation between the test compound and the portion of the region of BiP identified to interact with a Tau protein, followed by computationally analysing the results of the fitting operation to quantify the association between the test compound and the BiP protein. Preferably, the computer modelling system is supplied with a set of structure coordinates for a library of test compounds.

In another embodiment there is provided a kit including:

a nucleic acid, vector or construct, or cell as described above;

written instructions for use in a method described above.

Further aspects of the present invention and further embodiments of the aspects described in the preceding paragraphs will become apparent from the following description, given by way of example and with reference to the accompanying drawings.

BRIEF DESCRIPTION OF THE DRAWINGS

FIG. 4C: By 4 weeks of age, K3 mice develop a strong motor impairment characterised by a tremor, hind limb clenching and postural instability. The severeness of the motor impairment can be assessed using the Rota Rod, where mice are placed on a rotating rod and the longest time each mouse can remain on the rotating rod is recorded. This analysis demonstrates that in the first week of testing, when the mice are 4 weeks of age, male K3.Sil1+/− and K3.Sil1−/− mice perform better on the Rota Rod compared to their K3 control littermates. No significant differences are observed in the female mice.

FIG. 4D: Brain slices from these mice were also analysed using silver staining to detect the bundled axons of cerebellar basket cells that form Pinceau terminals (arrow) around Purkinje cells. Aged K3 mice show a pronounced degeneration of Pinceau terminals, as demonstrated by the lack of silver-positive axons (arrow head) compared to both wild type controls and Sil1−/− mice. However, there is only a moderate reduction in the loss of Pinceau terminals in K3.Sil1+/− mice, and Pinceau terminals are normal in K3.Sil1−/− mice, compared to controls.

FIG. 5: The nucleotide sequence of human Sil1 (SEQ ID NO: 1). The nucleotide sequence encoding the ER targeting region is underlined. The nucleotide sequence encoding the ER retention region is shown in bold and italics.

FIG. 6: The amino acid sequence of human Sil1 (SEQ ID NO: 2).

FIG. 7: The amino acid sequence of human BiP (SEQ ID NO: 3).

FIG. 8: The amino acid sequence of human Tau (SEQ ID NO: 4).

DETAILED DESCRIPTION OF THE EMBODIMENTS

Figure 1A:
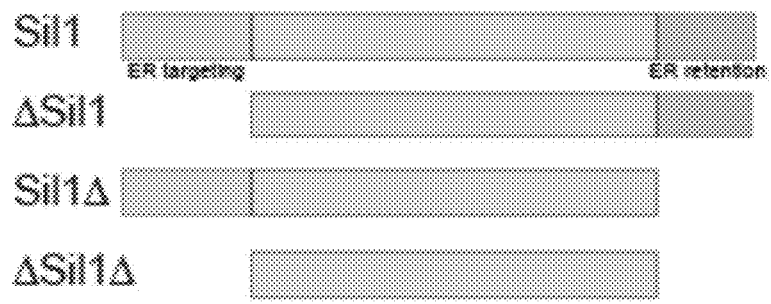
FIG. 1A: The Sil1 sequence contains an ER targeting signal (shown at the N-terminal end) and an ER retention signal (shown at the C-terminal end). Sil1 constructs that lack either the ER targeting and/or retention signals were generated

It will be understood that the invention disclosed and defined in this specification extends to all alternative combinations of two or more of the individual features mentioned or evident from the text or drawings. All of these different combinations constitute various alternative aspects of the invention.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described.

It will be understood that the invention disclosed and defined in this specification extends to all alternative combinations of two or more of the individual features mentioned or evident from the text or drawings. All of these different combinations constitute various alternative aspects of the invention.

All of the patents and publications referred to herein are incorporated by reference in their entirety.

For purposes of interpreting this specification, terms used in the singular will also include the plural and vice versa.

As used herein, except where the context requires otherwise, the term "comprise" and variations of the term, such as "comprising", "comprises" and "comprised", are not intended to exclude further additives, components, integers or steps.

Without being bound by any theory or mode of action it is believed that in normal physiology the cytoplasmic levels of Tau are maintained at non-pathological levels and in non-pathological forms by a balance of the production of Tau and its degradation. It is believed that Tau, at least in part, localizes to the endoplasmic reticulum by entering into a complex of Tau, Sil1 and BiP. Further, it is believed that Tau, Sil1 and BiP form a complex in normal physiology and that Sil1 promotes the ATPase activity of BiP to allow it to assist in the correct folding of Tau. The data herein shows that Tau interacts with Sil1 and also BiP.

However, when elevated levels of Sil1 are present in a cell, the activity of BiP is increased in the endoplasmic reticulum contributing to an increase in pathological Tau in the cytoplasm (e.g. Tau aggregates and phosphorylated Tau). The data herein shows that subjects with Alzheimer's disease and Pick's disease have elevated levels of Sil1. It is believed that this increase in pathological Tau in the cytoplasm, for example in the form of neurofibrillary tangles, is because the balance between Tau production and degradation is upset as increased BiP chaperone activity prevents Tau from being cleaved and cleared.

The reduction in Sil1 expression or activity or inhibition of the interaction of Tau with Sil1, Sil1 with BiP or BiP with Tau would reduce the formation of, or disrupt existing, complexes of Tau, Sil1 and BiP thereby leading to a reduction in the amount of misfolded Tau, insoluble Tau aggregates and/or reduction in the pathological phosphorylation of Tau. It is believed that a reduction in the complex of Tau, Sil1 and BiP that causes a reduction in the amount of misfolded Tau in the cytoplasm may be due to an increased cleavage of Tau and then clearance of the cleaved Tau fragments. As shown in the data herein a reduction in Sil1 in two mouse models of tauopathy leads to an increase in Tau cleavage and prevention of neuronal loss.

The inventors have developed methods and assays for determining whether a compound is likely to be useful in treating a tauopathy. The methods and assays are also useful to identify a compound as a candidate, for example a lead candidate, in the development of a drug for the treatment of a tauopathy. The method is based on the concept that if it is possible to block the formation of a complex, or disrupt an existing complex, between Sil1, Tau and BiP in vivo that it should then be possible to reduce the levels of pathological phosphorylation of Tau and also reduce pathologically insoluble forms of Tau. Blocking or inhibiting the formation of a complex of Sil1, Tau and BiP may involve disrupting only one protein-protein interaction, e.g. between Sil1 and Tau, Si1 and BiP or Tau and BiP. Accordingly, the methods described herein are directed to identifying compounds that can inhibit, at least, one of these protein-protein interactions.

Accordingly, in some aspects methods utilize the affinity of (a) Si1 for Tau (or Tau for Sil1), (b) Sil1 for BiP (or BiP for Sil1) and/or (c) Tau for BiP (or BiP for Tau) to form an assay system whereby when any one or more of these protein-protein interactions occur a detectable signal is formed. The signal is not formed, for example, when Sil1 is not bound to Tau (or Tau is not bound to Sil1), an outcome that is likely where a compound is bound to either Tau or Sil1 in such an arrangement that Sil1 is then precluded from binding to Tau (or Tau is then precluded from binding to Sil1). The same applies when Sil1 is not bound to BiP (or BiP to Sil1) or Tau to BiP (or BiP to Tau). Compounds that prevent or disrupt the molecular interaction of any of these proteins are identified as being is likely to be useful in treating a tauopathy because they are likely to reduce the levels of pathological phosphorylation of Tau, reduce pathologically insoluble forms of Tau, allow increased cleavage of Tau and/or allow increased clearance of Tau in vivo.

"Tauopathies" are a class of neurodegenerative disorders resulting from the pathological function of tau, primarily the pathological aggregation of tau into paired helical filaments (PHF) and eventually neurofibrillary tangles (NFT). A "tauopathy" one of the class of neurodegenerative disorders resulting from the pathological function of tau, primarily the pathological aggregation of tau into neurofibrillary tangles (NFT).

Examples of tauopathies include Alzheimer's disease, Amyotrophic lateral sclerosis/parkinsonism-dementia complex, Argyrophilic grain dementia, Corticobasal degeneration, Creutzfeldt-Jakob disease, Dementia pugilistica, Diffuse neurofibrillary tangles with calcification, Down's syndrome, Frontotemporal dementia with parkinsonism linked to chromosome 17a, Gerstmann-Sträussler-Scheinker disease, Hallervorden-Spatz disease, Myotonic dystrophy, Niemann-Pick disease, type C, Non-Guamanian motor neuron disease with neurofibrillary tangles, Pick's disease, Postencephalitic parkinsonism, Prion protein cerebral amyloid angiopathy, Progressive subcortical gliosis, Progressive supranuclear palsy, Subacute sclerosing panencephalitis and Tangle only dementia.

The invention provides a method for determining whether a compound is useful in the treatment of a tauopathy including the steps of:
  providing a test compound;
  providing a system that allows Sil1 expression or activity to be measured;
  contacting the system with the compound in conditions for permitting the compound to modulate Sil1 expression or activity;
  determining whether Sil1 expression or activity is modulated;

wherein a modulation, typically a reduction, in Sil1 expression or activity indicates that the compound is useful in the treatment of a tauopathy. Typically the system is an in vitro system or an in vivo system. The in vitro system may be a cell lysate or a recombinant system that allows Sil1 expression and/or activity to be measured. Preferably, the activity that is measured is ability of Sil1 to induce nucleotide exchange, the interaction of Sil1 and Tau, the interaction of Sil1 with BiP or the formation of a complex between Sil1, Tau and BiP. A reduction in the interaction of Sil1 and Tau, the interaction of Sil1 with BiP or the formation of a complex between Sil1, Tau and BiP indicates a reduction in Sil1 activity. Preferably, Sil1 expression is determined by measuring Sil1 protein levels or Sil1 mRNA levels.

The system may be a cell line or an animal model. The system may be a primary cell derived from a subject diagnosed with a tauopathy.

Preferably, the method further comprises determining whether the compound reduces neurofibrillary tangles.

The invention also provides for a method for identifying a compound as a candidate in the development of a drug to treat a tauopathy including the steps of:
  providing a test compound;
  providing a system that allows Sil1 expression or activity to be measured;
  contacting the system with the compound in conditions for permitting the compound to modulate Sil1 expression or activity;
  determining whether Sil1 expression or activity is modulated;

wherein a modulation, typically a reduction, in Sil1 expression or activity indicates that the compound is a candidate in the development of a drug to treat a tauopathy.

Any method or assay described herein can also be used for identifying a compound as a candidate in the development of a drug to treat a tauopathy.

In certain aspects of the invention there is provided a method for determining whether a compound is likely to be useful in treating a tauopathy. Generally the method determines the likelihood that a compound is useful in treating a tauopathy, again based on the understanding that if the compound binds to Sil1 or Tau in such a way as Sil1 is then precluded from binding to Tau, then pathological phosphorylation of Tau and pathologically insoluble forms of Tau should be reduced. The same understanding applies for Sil1 for BiP (or BiP for Sil1), Tau for BiP (or BiP for Tau) and a complex of Sil1, Tau and BiP. The same understanding applies if the compound reduces the activity or expression of Sil1.

Having identified compounds that are likely to reduce pathological phosphorylation of Tau and pathologically insoluble forms of Tau, in the form of compounds that, for example, block engagement of Sil1 with Tau with the method of invention, the relevant compounds identified with the method may then be screened in cell models or animal models in which pathological phosphorylation of Tau, cleavage of Tau, clearance of Tau and pathologically insoluble forms of Tau can be measured, or in which the modification of a pathology associated with pathological Tau, such as memory deficit or retention can be measured.

Methods and assays of the invention also include determining whether a compound is useful for inhibiting or reducing the formation of neurofibrillary tangles (NFT) or insoluble tau aggregates in a subject by performing the steps of any one of the methods or assays described herein. An absence of, or reduction in, a detectable signal as described herein indicates that the compound can inhibit or reduce the formation of neurofibrillary tangles (NFT) or insoluble tau aggregates. Alternatively, an absence of, or reduction in, the expression or activity of a protein as described herein indicates that the compound can inhibit or reduce the formation of neurofibrillary tangles (NFT) or insoluble tau aggregates.

A step of methods and assays of the invention generally involves providing a compound for which a capacity to reduce interaction between a Sil1 protein and a Tau protein is to be determined (or a Sil1 protein and a BiP protein, or a BiP protein and a Tau protein, or a complex of a Sil1 protein, a Tau protein and a BiP protein). The method also includes providing a compound for which a capacity to reduce the function of Sil1 without interfering with the molecular interaction between Sil1 and BiP is to be determined, for example, the capacity of the compound to modulate, typically reduce, the nucleotide exchange function of Sil1 is to be determined, or reduce expression of the Sil1 gene. Generally the compound will be provided in the form of a chemical library or fraction thereof. The compound may be one which has already found therapeutic application. Typically the compound is provided in serial dilutions for use in the method of invention, thereby providing for a standard curve against which efficacy for blocking of, for example, Sil1/Tau interaction can be determined against controls. In certain embodiments of the invention the test compound is a small molecule, nucleic acid (DNA, RNA, microRNA, siRNA, shRNA) peptide or a peptidomimetic. A 'peptidomimetic' is a synthetic chemical compound that has substantially the same structure and/or functional characteristics of a peptide of the invention, the latter being described further herein. Typically, a peptidomimetic has the same or similar structure as a peptide of the invention. A peptidomimetic generally contains at least one residue that is not naturally synthesised. Non-natural components of peptidomimetic compounds may be according to one or more of: a) residue linkage groups other than the natural amide bond ('peptide bond') linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like.

As used herein, the term "contacting" refers to the bringing together or combining of molecules such that they are within a distance for allowing of intermolecular interactions such as the non-covalent interaction between a two peptides or one protein and a compound. In some embodiments, contacting occurs in solution phase in which the combined or contacted molecules are dissolved in a common solvent and are allowed to freely associate. In some embodiments, the contacting can occur within a cell or in a cell-free environment. In some embodiments, the cell-free environment is the lysate produce from a cell. In some embodiments, a cell lysate may be a whole-cell lysate, nuclear lysate, cytoplasm lysate, and combinations thereof. In some embodiments, the cell-free lysate is only lysate obtained from a nuclear extraction and isolation wherein the nuclei of a cell population are removed from the cells and then lysed. In some embodiments, the nuclei are not lysed, but are still considered to be a cell-free environment. The interacting molecules can also be mixed such as through vortexing, shaking, and the like.

The next step generally involves the provision of a Sil1 protein and a Tau protein (or a Sil1 protein and a BiP protein, or a BiP protein and a Tau protein, or a Sil1 protein, Tau protein and a BiP protein). Typically the Sil1, Tau and BiP proteins are based on human sequences of these proteins, although in some embodiments, the sequences may be mammalian sequences, and particularly in circumstances where the proteins are expressed in non-human cell lines. Alternatively, this step of a method of the invention involves providing a system that allows Sil1 expression or activity to be measured. Typically the system is an in vitro system or an in vivo system. The in vitro system may be a cell lysate or a recombinant system that allows Sil1 expression and/or activity to be measured. Preferably, the activity that is measured is ability of Sil1 to induce nucleotide exchange. Preferably, Sil1 expression is determined by measuring Sil1 protein levels or Sil1 mRNA levels.

The human Tau protein can occur in the brain in six alternatively spliced isoforms. The longest human Tau isoform, htau40 (441 aa) (NCBI sequence reference NP_005901), comprises an amino-terminal projection domain (PD; also known as Tau projection domain or projection domain of Tau), followed by a microtubule binding domain (MTB) with four repeats and a carboxy-terminal tail. The amino-terminal projection domain of Tau protrudes from the microtubule surface when the Tau protein is bound to microtubules.

htau40 can also be referred to as 2N4R as it contains 2 amino-terminal inserts (2N) and 4 microtubule-binding repeats (4R). The two amino-terminal inserts are encoded by two alternatively spliced exons, E2 and E3, and encode 29 amino acids each. The various isoforms of the Tau protein arise from alternative splicing of exon 2, 3 and 10. The isoforms differ in either 0, 1 or 2 inserts of the 29 amino acid amino-terminal part and three or four microtubule-binding repeats. The isoforms of human Tau are summarised below:

The 0N3R isoform is 352 amino acids in length (NCBI sequence reference NP_058525.1), with the amino-terminal projection domain being 197 amino acids.

The 0N4R isoform is 383 amino acids in length (NCBI sequence reference NP_058518.1), with the amino-terminal projection domain being 197 amino acids.

The 1N3R isoform is 383 amino acids in length, with the amino-terminal projection domain being 226 amino acids.

The 1N4R isoform is 412 amino acids in length, with the amino-terminal projection domain being 226 amino acids.

The 2N3R isoform is 410 amino acids in length, with the amino-terminal projection domain being 255 amino acids.

The 2N4R isoform is 441 amino acids in length, with the amino-terminal projection domain being 255 amino acids.

The amino acid sequence of human Tau isoforms can be found in publicly available databases, for example those supported by NCBI (National Center for Biotechnology Information), including GenBank®.

The nucleotide sequence of human Sil1 can be found in publicly available database, for example, via NCBI sequence reference NM_001037633.1 or NM_022464.4 and the corresponding amino acid sequence via NCBI sequence reference NP_001032722.1 or NP_071909.1.

The nucleotide sequence of human BiP (also known as GRP78) can be found in publicly available database, for example, via NCBI sequence reference NM_005347.4 and the corresponding amino acid sequence via NCBI sequence reference NP_005338.1.

It will be recognised that sequences that have some homology, but not complete identity with any one of the above Sil1, Tau and BiP sequences could be used in place of any one of the above Sil1, Tau and BiP sequences, provided that the relevant sequences at least have the sequence specificity necessary to provide for the interaction between Sil1 and Tau (or Sil1 and BiP, or BIP and Tau, or a complex of Sil1, Tau and BiP).

As used herein, the Sil1 protein includes, consists essentially of or consists of an amino acid sequence, domain or region that mediates non-covalent association with Tau and/or BiP. Preferably, the Sil1 protein as defined herein does not include the full length Sil1 protein, however the Sil1 protein includes all amino acids of the full length Sil1 protein that mediate the native association with Tau and/or BiP. Typically, the Sil1 protein includes, consists essentially of or consists of all amino acids of the full length Sil1 protein except for amino acid sequences that target Sil1 to the endoplasmic reticulum and/or amino acid sequences that retain Sil1 in the endoplasmic reticulum. Preferably, the amino acid sequence of the Sil1 protein includes, consists essentially of or consists of any amino acid sequence that mediates binding to Tau with a similar affinity to amino acids 31 to 449 of human Sil1 (SEQ ID NO: 2). Preferably, the amino acid sequence of the Sil1 protein includes, consists essentially of or consists of any amino acid sequence that mediates binding to BiP with a similar affinity to amino acids 113 to 421 of human Sil1 (SEQ ID NO: 2). Those amino acids of Sil1 which do not mediate the interaction with Tau and/or BiP may be substitutable. Even more preferably, the Sil1 protein includes, consists essentially of or consists of amino acids 31 to 449 of human Sil1 (SEQ ID NO: 2). Even more preferably, the Sil1 protein includes, consists essentially of or consists of amino acids 113 to 421 of human Sil1 (SEQ ID NO: 2) The Sil1 protein may include, consist essentially of or consist of an amino acid sequence that is 60, 70, 80, 90, 91, 92, 93, 94, 95, 96, 97, 98, 99 or 100% identical to the sequence shown in SEQ ID NO: 2.

In one embodiment, the Sil1 protein is isolated, recombinant, purified, substantially purified, synthetic or a peptidomimetic.

As used herein, the Tau protein includes, consists essentially of or consists of an amino acid sequence, domain or region that mediates non-covalent association with Sil1 and/or BiP. Preferably, the Tau protein as defined herein does not include the full length Tau protein, however the Tau protein includes all amino acids of the full length Tau protein that mediate the association with Sil1 and/or BiP.

By utilizing only the minimal region of Sil1 that mediates binding to Tau and the minimal region of Tau binding to Sil1, it is more likely that a method of the invention will identify inhibitors that directly interfere with the non-covalent protein-protein interaction of Sil1 and Tau. The same applies for Sil1 and BiP, and BiP and Tau.

However, if more of the Sil1 protein than just the minimal region that mediates binding to Tau and if more of the Tau protein than just the minimal region that mediates the binding to Sil1 is used in the method of the invention then there is an increased likelihood that an inhibitor which has an allosteric mechanism will be identified. In this context allosteric means disruption of the interaction of Sil1 and Tau without directly competing with Sil1 binding to Tau or Tau binding to Sil1. The same applies for Sil1 and BiP and BiP and Tau.

In one embodiment, the Tau protein is isolated, recombinant, purified, substantially purified, synthetic peptide or a peptidomimetic.

As used herein, the BiP protein includes, consists essentially of or consists of an amino acid sequence, domain or region that mediates non-covalent association with the Sil1 and/or Tau. Preferably, the BiP protein does not include the full length BiP protein, however the BiP protein includes all amino acids of the full length BIP protein that mediate the native association with Sil1 and/or Tau. Typically, the BiP protein includes, consists essentially of or consists of all amino acids of the ATPase domain. Preferably, the amino acid sequence of the BiP protein includes, consists essentially of or consists of any amino acid sequence that mediates binding to Sil1 with a similar affinity to amino acids 43-426 of human BiP (SEQ ID NO: 3). Those amino acids of BiP which do not mediate the interaction with Sil1 may be substitutable. Even more preferably, the BiP protein includes, consists essentially of or consists of amino acids 43-426 of human BiP (SEQ ID NO: 3). The Sil1 protein may include, consist essentially of or consist of an amino acid sequence that is 60, 70, 80, 90, 91, 92, 93, 94, 95, 96, 97, 98, 99 or 100% identical to the sequence shown in SEQ ID NO: 3.

"Percent (%) amino acid sequence identity" or "percent (%) identical" with respect to a peptide or polypeptide sequence, i.e. a peptide of the invention defined herein, is defined as the percentage of amino acid residues in a candidate sequence that are identical with the amino acid residues in the specific peptide or polypeptide sequence, i.e. a peptide of the invention, after aligning the sequences and introducing gaps, if necessary, to achieve the maximum percent sequence identity, and not considering any conservative substitutions as part of the sequence identity.

Those skilled in the art can determine appropriate parameters for measuring alignment, including any algorithms (non-limiting examples described below) needed to achieve maximal alignment over the full-length of the sequences being compared. When amino acid sequences are aligned, the percent amino acid sequence identity of a given amino acid sequence A to, with, or against a given amino acid sequence B (which can alternatively be phrased as a given amino acid sequence A that has or comprises a certain percent amino acid sequence identity to, with, or against a given amino acid sequence B) can be calculated as: percent amino acid sequence identity=X/Y100, where X is the number of amino acid residues scored as identical matches by the sequence alignment program's or algorithm's alignment of A and B and Y is the total number of amino acid residues in B. If the length of amino acid sequence A is not equal to the length of amino acid sequence B, the percent amino acid sequence identity of A to B will not equal the percent amino acid sequence identity of B to A.

In calculating percent identity, typically exact matches are counted. The determination of percent identity between two sequences can be accomplished using a mathematical algorithm. A nonlimiting example of a mathematical algorithm utilized for the comparison of two sequences is the algorithm of Karlin and Altschul (1990) Proc. Natl. Acad. Sci. USA 87:2264, modified as in Karlin and Altschul (1993)

Proc. Natl. Acad. Sci. USA 90:5873-5877. Such an algorithm is incorporated into the BLASTN and BLASTX programs of Altschul et al. (1990) J. Mol. Biol. 215:403. To obtain gapped alignments for comparison purposes, Gapped BLAST (in BLAST 2.0) can be utilized as described in Altschul et al. (1997) Nucleic Acids Res. 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. Alignment may also be performed manually by inspection. Another non-limiting example of a mathematical algorithm utilized for the comparison of sequences is the ClustalW algorithm (Higgins et al. (1994) Nucleic Acids Res. 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif.). After alignment of amino acid sequences with ClustalW, the percent amino acid identity can be assessed. A non-limiting example of a software program useful for analysis of ClustalW alignments is GENEDOC™. GENEDOC™ allows assessment of amino acid (or DNA) similarity and identity between multiple proteins. Another non-limiting example of a mathematical algorithm utilized for the comparison of sequences is the algorithm of Myers and Miller (1988) CABIOS 4:11-17. Such an algorithm is incorporated into the ALIGN program (version 2.0), which is part of the GCG Wisconsin Genetics Software Package, Version 10 (available from Accelrys, Inc., 9685 Scranton Rd., San Diego, Calif., USA). When utilizing the ALIGN program for comparing amino acid sequences, a PAM 120 weight residue table, a gap length penalty of 12, and a gap penalty of 4 can be used.

In accordance with the a further step of methods or assays of the invention, the Sil1 and/or Tau proteins are adapted to form a detectable signal when the Sil1 protein is bound to the Tau protein. Alternatively, the Sil1 and/or BiP proteins are adapted to form a detectable signal when the Sil1 protein is bound to the BiP protein. Alternatively, the BiP and/or Tau proteins are adapted to form a detectable signal when the BIP protein is bound to the Tau protein. Alternatively, the Sil1, Tau and BiP proteins are adapted to form a detectable signal when a complex is formed between Sil1, Tau and BiP. A "Detectable signal" as used herein refers to any observable effect including enzymatic activity, bioluminescence, chemiluminescence, fluorescence or absorbance. The observable effect may be detected by affinity purification mass spectrometry, genetic test systems such as yeast two hybrid, mating based split ubiquitin system, fluorescence resonance energy transfer (FRET), bioluminescence resonance energy transfer (BRED, atomic force microscopy, plasmon resonance such as quantitative surface plasmon resonance, calorimetry, GST pull-down, co-immunoprecipitation and NMR. The detectable signal may be ADP or ATP/ADP levels as a measure of BiP ATPase activity. Any of these assays can be utilised to determine whether Sil1 expression or activity is modulated or whether a signal is formed or a complex is present.

The detectable signal may arise from a split reporter system. Examples of split reporter systems include ubiquitin (Johnsson, N.; Varshaysky, A. Proc Natl Acad Sci USA 1994, 91, 10340-4.), beta-galactosidase (Rossi, F.; Charlton, C. A.; Blau, H. M. Proc Natl Aced Sci USA 1997, 94, 8405-10.), dihydrofolate reductase (Pelletier, J. N.; Campbell-Valois, F. X.; Michnick, S. W. Proc Nati Aced Sci USA 1998, 95, 12141-6.), beta-lactamase (Galarneau, A.; Primeau, M.; Trudeau, L. E.; Michnick, S. W. Nat Biotechnol 2002, 20, 619-22.), GFP (Ghosh, I.; Hamilton, A. D.; Regan, L. J. Am. Chem. Soc. 2000, 122, 5658-5659), GFP-variants (MacDonald, M. L.; Lamerdin, J.; Owens, S.; Keon, B. H.; Bilter, G. K.; Shang, Z.; Huang, Z.; Yu, H.; Dias, J.; Minami, T.; Michnick, S. W.; Westwick, J. K. Nat Chem Biol 2006, 2, 329-337. Hu, C. D.; Kerppola, 1. K. Nat Biotechnol, 2003, 21, 539-45.), firefly luciferase (Paulmurugan, R; Umezawa, Y.; Gambhir, S. S. Proc Natl Acad Sci USA 2002, 99, 15608-13) and Gaussia luciferase (Remy, I.; Michnick, S. W. Nat Methods 2006, 3, 977-9).

Fragments of green fluorescent protein (GFP), each having no capacity for fluorescence alone, but with capacity for fluorescence when combined, may be linked to one or other of Sil1 and Tau, so that when Sil1 is bound to Tau (or Tau to Sil1), the fragments of GFP are brought together, ostensibly re-assembling the GFP thereby generating a fluorescent signal. The same applies for methods involving Sil1 and BiP, BiP and Tau, and Sil1, Tau and BiP.

It will be understood that the detectable signal may include enzymatic activity, bioluminescence, chemiluminescence, fluorescence or absorbance, in which case fragments of the relevant signalling moiety, or component parts that give rise to signalling can be provided on Sil1 and/or Tau. The same applies for methods involving Sil1 and BiP, BiP and Tau, and Sil1, Tau and BiP.

Preferably, the Sil1 protein and Tau protein (or Sil1 and BiP, or BiP and Tau) are each fused to a portion of a GFP molecule such that association of the Sil1 and Tau protein (or Sil1 and BiP, or BiP and Tau) reconstitute or reassemble the GFP allowing for fluorescence to be generated. Preferably, the Sil1 protein is joined, operably linked, or fused to N-GFP and the Tau protein is joined to C-GFP, or vice versa.

In one embodiment, determining whether a detectable signal is generated includes determining the quality or quantity of the detectable signal. Preferably, determining whether a signal is generated includes determining whether a signal is reduced.

In a preferred method or assay of the invention, surface plasmon resonance (SPR) is used. This may be in conjunction with an SPR imaging system that allows detection of protein-protein interactions. Typically, the SPR is conducted in a high throughput format by spotting proteins using a protein arrayer onto a suitable surface, such as gold thin film. An exemplary SPR imaging system and high throughput format is described in Jung et al. (2005) Proteomics, 5, 4427-4431. An advantage of the SPR method is that the protein-protein interactions can be analysed in high-throughput format without the use of labels. Further, the ability of the test compound to interact directly with the protein coated on the surface, e.g. the GST-Tau in Example 6, can be tested.

Typically the Sil1, Tau and/or BiP protein(s) are provided in a cell by expression of a Sil1, Tau and/or BiP-encoding construct in a cell. Any eukaryotic cell line can be used for this purpose, depending on the type of construct used for expression of Sil1, Tau and/or BiP protein. Typically the cell line is negative for Sil1, Tau and/or BiP.

Where the Sil1, Tau and/or BiP proteins are provided by recombinant means, there is requirement for nucleic acids, constructs and cells containing same. Therefore, in one embodiment, there is provided a nucleic acid that includes, consists essentially of or consists of a nucleotide sequence that encodes a Sil1 protein as described herein. Preferably the nucleotide sequence is at least 60, 70, 80, 90, 91, 92, 93, 94, 95, 96, 97, 98, 99 or 100% identical to the sequence shown in SEQ ID NO: 1 or a functionally active fragment or variant thereof.

In a further embodiment, there is provided a nucleic acid that includes, consists essentially of or consists of a nucleotide sequence that encodes a Tau protein as described herein. Preferably the nucleotide sequence is at least 60, 70, 80, 90, 91, 92, 93, 94, 95, 96, 97, 98, 99 or 100% identical to a sequence described herein or a sequence that encodes the amino acid sequence of SEQ ID NO: 4 or a functionally active fragment or variant thereof.

In a further embodiment, there is provided a nucleic acid that includes, consists essentially of or consists of a nucleotide sequence that encodes a BiP protein as described herein. Preferably the nucleotide sequence is at least 60, 70, 80, 90, 91, 92, 93, 94, 95, 96, 97, 98, 99 or 100% identical to a sequence described herein or a sequence that encodes the amino acid sequence of SEQ ID NO: 3 or a functionally active fragment or variant thereof.

In another embodiment, there is provided a genetic construct including a nucleic acid as described herein. The genetic construct allows expression of the Sil1 protein, Tau protein and/or BiP protein in a cell.

In a further embodiment, there is provided a cell including a genetic construct or nucleic acid as described herein. Preferably the cell is a neuronal cell. The neuronal cell may be an immortalized or transformed neuronal cell or a primary neuronal cell. A primary neuronal cell is a neuronal cell that can differentiate into other types of neuronal cells, such as glial cells. A neuronal cell includes unipolar, pseudounipolar, bipolar and multipolar neurons, Basket cells, Betz cells, medium spiny neurons, Purkinje cells, pyramidal cells, Renshaw cells and granule cells. The cell may also be other cells found in the brain including glial cells, such as microglia, astrocytes, oligodendrocytes. The cell may be macrophages have the capacity to or have entered the brain. The cells may be other cells of the central nervous system. The cell may be a cell line of human or non-human origin including neuroblastoma cells or any cell lines available from the ATCC (American Type Culture Collection). An example of a neuroblastoma cell line is SH-SY5Y.

In another embodiment the Sil1 protein, Tau protein and BiP protein are recombinant, purified, isolated or synthetic and incubated under conditions that allow non-covalent association. Typically the conditions that allow non-covalent association are physiological conditions, or the like, as described further herein.

The next step of the methods or assays of the invention generally involves contacting the Sil1 protein and the Tau protein with the compound in conditions for permitting the compound to bind to either or both of the Sil1 protein and Tau protein, thereby inhibiting the binding of the Sil1 protein to the Tau protein when the compound is bound to either or both of Sil1 protein and Tau protein. Where a cell is used to provide Sil1 and Tau, the Sil1 and Tau may be bound to one another before they are contacted with the compound, in accordance with the third step of the method. In other methods of the invention this step involves contacting the Sil1 protein and the BiP protein with the compound in conditions for permitting the compound to bind to either or both of Sil1 protein and BIP protein. In other methods of the invention this step involves contacting the Tau protein and BiP protein with the compound in conditions for permitting the compound to bind either the Tau protein or BiP protein. In other methods of the invention this step involves contacting a system or Sil1 protein with the compound in conditions for permitting the compound to bind to Sil1 and inhibit its function with or without inhibiting the binding of Sil1 and BiP. Preferably, the system allows Sil1 expression or activity to be measured. Typically the system is an in vitro system or an in vivo system. The in vitro system may be a cell lysate or a recombinant system that allows Sil1 expression and/or activity to be measured. Preferably, the activity that is measured is ability of Sil1 to induce nucleotide exchange. Preferably, Sil1 expression is determined by measuring Sil1 protein levels or Sil1 mRNA levels.

The next step in methods or assays of the invention involve determining whether a detectable signal is formed from binding of Sil1 protein to Tau protein (or Sil1 protein binding to BiP protein, or Tau protein to BiP protein, or a complex of a Sil1 protein, a Tau protein and a BIP protein, or from the expression or activity of Sil1). The means required for this determination are based on the type of signal to be generated. In an embodiment of the invention when Sil1 and Tau proteins are fused to a component of GFP such that the binding of Sil1 protein to Tau protein permits reassembly or reconstitution of GFP, the detection method may be fluorescent microscopy. The same applies for Sil1 and BiP and BiP and Tau.

According to the method, where there is an absence or reduction of a detectable signal, this indicates that the compound inhibits the binding of the Sil1 protein to the Tau protein and therefore indicates a likelihood that the compound is useful in treating a tauopathy. The same applies for Sil1 and BiP, and BiP and Tau.

Preferably, control assays are run concurrently with a method of the invention to minimise the identification of false positives. For example, the test compound is incubated in the absence of the Sil1 protein and Tau protein and instead only in the presence of the two components which act as a split reporter system that when associated generate the detectable signal. This control assay allows for the determination of whether a test compound disrupts the interaction of the components of the split reporter system directly by either binding to one or both of the components of the split reporter system rather than by disrupting the non-covalent association between the Sil1 protein and Tau protein. The same applies for Sil1 and BiP, and BiP and Tau. A control assay may also include performing a method of the invention in the absence of the test compound to determine a level of detectable signal from which any reduction in the presence of a test compound can be determined. Alternatively, a detectable signal can be determined before and after the test compound is contacted to the Tau, Sil1 and/or BiP protein or system that allows a reduction in the detectable signal to be determined.

In any method or assay of the invention described herein there also includes the steps of:
  providing conditions for permitting formation, or recovery, of the detectable signal; and
  determining whether a detectable signal is formed,
wherein formation of the detectable signal determines that the compound is likely to selectively reduce (a) Sil1 expression or activity. (b) the formation of a complex between Sil1, Tau and BiP proteins, (c) the binding of Sil1 protein to Tau protein, (d) the binding of Sil1 protein to BiP protein, and/or (e) the binding of Tau protein to BiP protein.

Formation of, or recovery of the detectable signal determines that the compound does not permanently disrupt the expression, activity or interaction. Further, recovery of the detectable signal indicates that the compound reduces the pathophysiological expression, activity or interaction to a non-cytotoxic level. If the method is conducted intracellularly then recovery of the signal also indicates that the compound is not cytotoxic in a Sil1, Tau and/or BiP independent manner. Recovery of the detectable signal includes restoration or regeneration of the detectable signal to a level or degree that is similar or the same as the detectable signal that would occur in the absence of the compound.

Providing conditions for the formation of, or recovery of the detectable signal after the contacting the compound is intended to determine whether the compound can dissociate from its target over time thereby allowing (a) Sil1 expression or activity, (b) the formation of a complex between Sil1, Tau and BiP proteins, (c) the binding of Sil1 protein to Tau protein, (d) the binding of Sil1 protein to BiP protein, and/or (e) the binding of Tau protein to BiP protein. The conditions which allow this to occur are typically physiological conditions, or the like, thereby allowing determination as to whether the inhibitor interferes with only the pathophysiological interactions mediated by Sil1, Tau and/or BiP or also inhibits the normal physiological interactions of Sil1, Tau and/or BIP. Physiological conditions may include one or more of the following, a temperature range of 20 to 40 degrees Celsius, preferably about 37 degrees Celsius, atmospheric pressure of 1, pH of 6 to 8, preferably a pH of 7.0 to 7.5, glucose concentration of 1 to 20 mM, atmospheric oxygen concentration and about 10% carbon dioxide concentration. These conditions particularly apply when the Sil1, Tau and/or BiP protein are derived from a mammalian sequence and/or the assay is performed in a mammalian system, e.g. a mammalian cell, or lysate from a mammalian cell. These conditions also apply if the assay is conducted in vitro, non-intracellular, cell free environment.

A method or assay of the invention can be conducted in high throughput. The method or assay may be conducted in a cell or in a cell-free environment, such as in a cell lysate or in an in vitro condition. For example, the assay may be performed by using 96, 384 or 1536 well plates and the inhibitor may be from a chemical library. Typically, the chemical library is one which has been designed to inhibit protein-protein interactions and/or includes compounds that are known to inhibit protein-protein interactions or are already approved for clinical use in humans or animals.

The present invention also provides a method for identifying a compound for the treatment of a tauopathy including the steps of:
  supplying a computer modelling application with a set of structure co-ordinates for a Sil1 protein, wherein the Sil1 protein comprises at least a portion of the region identified to interact with a Tau protein;
  supplying the computer modelling application with a set of structure coordinates for a test compound; and
  determining whether the test compound is expected to bind to the Sil1 protein on the region identified to interact with a Tau protein
wherein binding of the test compound to Sil1 protein on the region identified to interact with a Tau protein is indicative of the test compound being useful in the treatment of a tauopathy. Preferably, determining whether the test compound is expected to bind to the Sil1 protein includes performing a fitting operation between the test compound and the portion of the region of Sil1 identified to interact with a Tau protein, followed by computationally analysing the results of the fitting operation to quantify the association between the test compound and the Sil1 protein. Preferably, the computer modelling system is supplied with a set of structure coordinates for a library of test compounds.

This method of the invention can also be performed by supplying a computer modelling application with a set of structure co-ordinates for a Sil1 protein, wherein the Sil1 protein comprises at least a portion of the region identified to interact with a BIP protein. This method of the invention can also be performed by supplying a computer modelling application with a set of structure co-ordinates for a BiP protein, wherein the BiP protein comprises at least a portion of the region identified to interact with a Sil1 protein. This method of the invention can also be performed by supplying a computer modelling application with a set of structure co-ordinates for a BiP protein, wherein the BiP protein comprises at least a portion of the region identified to interact with a Tau protein.

The present invention also provides a method for identifying a compound for the treatment of a tauopathy including the steps of:
  supplying a computer modelling application with a set of structure co-ordinates for a Sil1 protein, wherein the Sil1 protein comprises at least a portion of the region identified to interact with a Tau protein;
  supplying the computer modelling application with a set of structure coordinates for a test compound;
  evaluating the potential binding interaction between the test compound and the region of Sil1 identified to interact with a Tau protein;
  structurally modifying the test compound to present a set of structure coordinates for the modified test compound; and
  determining whether the modified test compound is expected to bind to the Sil1 protein on the region identified to interact with a Tau protein
wherein binding of the modified test compound to Sil1 protein on the region identified to interact with a Tau protein is indicative of the test compound being useful in the treatment of a tauopathy. This method of the invention can also be performed by supplying a computer modelling application with a set of structure co-ordinates for a Sil1 protein, wherein the Sil1 protein comprises at least a portion of the region identified to interact with a BiP protein. This method of the invention can also be performed by supplying a computer modelling application with a set of structure co-ordinates for a BiP protein, wherein the BiP protein comprises at least a portion of the region identified to interact with a Sil1 protein. This method of the invention can also be performed by supplying a computer modelling application with a set of structure co-ordinates for a BiP protein, wherein the BiP protein comprises at least a portion of the region identified to interact with a Tau protein.

Instead of supplying the computer modelling application with a set of structure coordinates for a test compound, a compound can be designed de novo by building a set of structure coordinates using applications known to those in the field.

The present invention also includes a method for producing a compound for the treatment of a tauopathy, the method including the steps of chemically or enzymatically synthesizing a compound, the compound having been designed by a method including the steps of
  supplying a computer modelling application with a set of structure co-ordinates for a Sil1 protein, wherein the Sil1 protein comprises at least a portion of the region identified to interact with a Tau protein;
  supplying the computer modelling application with a set of structure coordinates for a test compound; and determining whether the test compound is expected to bind to the Sil1 protein on the region identified to interact with a Tau protein wherein binding of the test compound to Sil1 protein on the region identified to interact with a Tau protein is indicative of the test compound being useful in the treatment of a tauopathy. This method of the invention can also be performed by supplying a computer modelling application with a set of structure co-ordinates for a Sil1 protein, wherein the Sil1 protein comprises at least a portion of the region identified to interact with a BiP protein. This method of the invention can also be performed by supplying a computer modelling application with a set of structure co-ordinates for a BiP protein, wherein the BiP protein comprises at least a portion of the region identified to interact with a Sil1 protein. This method of the invention can also be performed by supplying a computer modelling application with a set of structure co-ordinates for a BiP protein, wherein the BiP protein comprises at least a portion of the region identified to interact with a Tau protein.

The present invention also includes a method for identifying a compound for the treatment of a tauopathy including the steps of:

selecting a potential Sil1 interacting compound by performing rational drug design with a three-dimensional structure of a Sil1 protein, wherein the Sil1 protein includes at least a portion of the region identified to interact with a Tau protein, wherein selecting is performed in conjunction with computer modelling;

contacting the potential Sil1 interacting compound with a Sil1 protein; and detecting an affinity for binding of the potential Sil1 interacting compound with the Sil1 protein, wherein a compound is identified as useful in the treatment of a tauopathy if the affinity for the Sil1 protein is the same or greater than the affinity of a Tau protein for the Sil1 protein. This method of the invention can also be performed by supplying a computer modelling application with a set of structure co-ordinates for a Sil1 protein, wherein the Sil1 protein comprises at least a portion of the region identified to interact with a BiP protein. This method of the invention can also be performed by supplying a computer modelling application with a set of structure co-ordinates for a BiP protein, wherein the BiP protein comprises at least a portion of the region identified to interact with a Sil1 protein. This method of the invention can also be performed by supplying a computer modelling application with a set of structure co-ordinates for a BiP protein, wherein the BiP protein comprises at least a portion of the region identified to interact with a Tau protein.

Whether a compound binds a Sil1 protein at a site on the Sil1 protein that is involved in the interaction with a Tau or BiP protein may be examined through the use of computer modelling using a docking program such as GRAM, DOCK, or AUTODOCK (See for example, Morris et al., J. Computational Chemistry, 19:1639-1662 (1998)). This procedure can include in silico fitting of potential compounds to the Sil1 crystal structure to ascertain how well the shape and the chemical structure of the compound will complement or interfere with the interaction with BiP or affect the nucleotide exchange factor activity of Sil1 (Bugg et al., Scientific American, December: 92-98 (1993); West et al., TIPS, 16:67-74 (1995)). As those skilled in the art will understand, computer programs can also be employed to estimate the attraction, repulsion, and steric hindrance of the compound to the site on Sil1. Generally the tighter the fit (e.g., the lower the steric hindrance, and/or the greater the attractive force) the more potent the compound will be since these properties are consistent with a tighter binding constant. The same applies for determining whether a compound binds a BiP protein at a site on the BiP protein that is involved in the interaction with a Tau or Sil1 protein.

The structural co-ordinates for the human BiP ATPase domain can be found in the Protein Data Bank via accession number 3QFU. The structural co-ordinates for the Sil1-BiP complex can be found in the Protein Data Bank under accession code 3QML, from which the co-ordinates for the Sil1 protein can be derived.

Furthermore, the more specificity in the design of a compound the more likely that the compound will not interfere with the properties of other proteins. This will minimize potential side-effects due to unwanted interactions with other proteins.

Whether a compound binds a Sil1 protein at a site on the Sil1 protein that is involved in the interaction with a Tau protein or BiP protein may be may be carried out in silico using a variety of molecular modelling software algorithms including, but not limited to, DOCK, ALADDIN, CHARMM simulations, AFFINITY, C2-LIGAND FIT, Catalyst, LUDI, CAVEAT, and CONCORD. (Brooks, et al. CHARMM: a program for macromolecular energy, minimization, and dynamics calculations. (*J Comp. Chem* 1983, 4:187-217; E. G. Meng, B. K. Shoichet & I. D. Kuntz. Automated docking with grid-based energy evaluation. *J Comp Chem* 1992, 13:505-524). The same algorithms can be used to determine whether a compound binds to a BiP protein at a site on the BIP protein that is involved in the interaction with a Tau protein or a Sil1 protein.

Alternatively, a compound that binds a Sil1 protein at a site on the Sil1 protein that is involved in the interaction with a Tau protein may be obtained by screening a random peptide library produced by a recombinant bacteriophage (Scott and Smith, Science, 249:386-390 (1990); Cwirla et al., Proc. Natl. Acad. Sci., 87:6378-6382 (1990); Devlin et al., Science, 249:404-406 (1990)) or a chemical library, or the like. A compound selected in this manner can be then be systematically modified by computer modeling programs until one or more promising compounds are identified. A random peptide library can be used to obtain a compound that binds to a BiP protein at a site that is involved in the interaction with a Tau protein or a Sil1 protein.

Once a compound is identified, it can be either selected from a library of chemicals as are commercially available from most large chemical companies or alternatively the compound may be synthesized de novo.

In yet further embodiments, the in silico methods are molecular modeling methods wherein 3-dimensional models of macromolecules or ligands are generated. In other embodiments, the in silico methods comprise computationally assessing ligand binding interactions.

To be a viable drug candidate, the compound identified or designed according to a method of the invention should be capable of structurally associating with at least part of a Sil1 protein that has been identified to interact with a Tau protein or BiP protein (or at least part of a BiP protein that has been identified to interact with a Sil1 protein or Tau protein), and must be able, sterically and energetically, to assume a conformation that allows it to associate with this region. Non-covalent molecular interactions important in this association include hydrogen bonding, van der Waals interactions, hydrophobic interactions, and electrostatic interactions. Conformational considerations include the overall three-dimensional structure and orientation of the test compound in relation to the region on Sil1 which interacts with a Tau protein or BiP protein, and the spacing between various functional groups of an test compound that directly interact with the region that interacts with a Tau protein or BIP protein.

Optionally, the potential binding of a test compound to a Sil1 protein, BiP protein or Tau protein is analyzed using computer modeling techniques prior to the actual synthesis and testing of the compound. If these computational experiments suggest insufficient interaction and association between it and the Sil1 protein, BiP protein or Tau protein, testing of the compound is not required. However, if computer modeling indicates a strong interaction, the molecule may then be synthesized and tested for its ability to bind to a Sil1 protein, BiP protein or Tau protein or interfere with the relevant molecular interaction or functions. Binding assays to determine if a compound (e.g., an inhibitor) actually interferes with a Sil1 protein interacting with a Tau protein (or a BiP protein interacting with a Sil1 protein, or a Tau protein interacting with a BiP protein, or a complex of a Sil1 protein, Tau protein and BiP protein) can also be performed and are well known in the art. Binding assays are described herein and may employ kinetic or thermodynamic methodology using a wide variety of techniques including, but not limited to, microcalorimetry, circular dichroism, capillary zone electrophoresis, nuclear magnetic resonance spectroscopy, fluorescence spectroscopy, and combinations thereof.

It will be understood that the methods and assays of the invention described herein, apply to characterization of one or more of the interactions between Sil1 and Tau, Sil1 and BiP, BiP and Tau, and Sil1, BiP and Tau, in the presence of a test compound.

It will be understood that these examples are intended to demonstrate these and other aspects of the invention and although the examples describe certain embodiments of the invention, it will be understood that the examples do not limit these embodiments to these things. Various changes can be made and equivalents can be substituted and modifications made without departing from the aspects and/or principles of the invention mentioned above. All such changes, equivalents and modifications are intended to be within the scope of the claims set forth herein.

Example 1

Figure 1B:
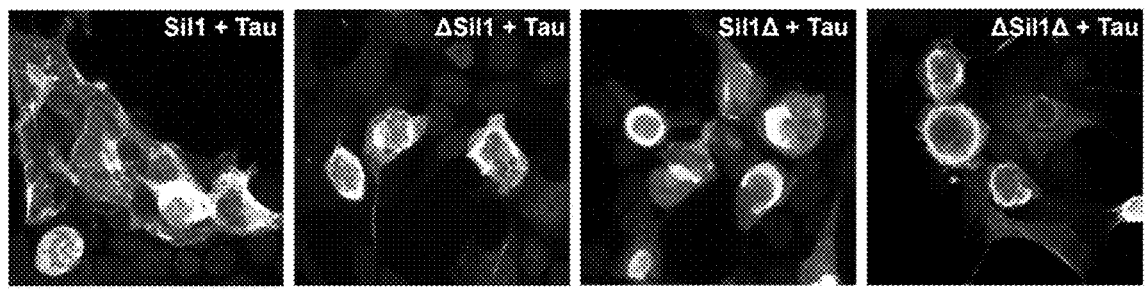
FIG. 1B: these were expressed together with human tau (hTau) or mutant human tau (P301 L-hTau) in cells (b).
Figure 1C:
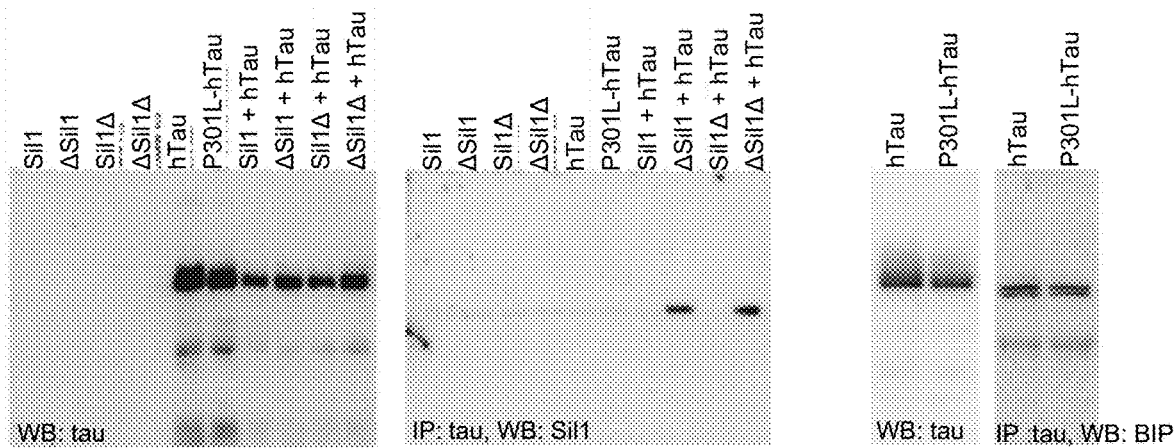
FIG. 1C Human tau protein was isolated from these cells by immunoprecipitation (IP) and then analysed by Western blotting (WB).

The protein BiP (also known as Grp78) is a molecular chaperone that carries out numerous essential functions in the endoplasmic reticulum (ER), such as protein folding and degradation. In order to carry out these functions efficiently, BiP requires the assistance of a protein known as Sil1. The Sil1 sequence contains an ER targeting signal (shown at the N-terminal end) and an ER retention sequence (shown at the C-terminal end). Sil1 constructs that lack either the ER targeting and/or retention signals were generated and these were expressed together with human tau (hTau) or mutant human tau (P301L-hTau) in cells (Sil1 stained in green and hTau in red. Yellow indicates colocalization). Human tau protein was isolated from these cells by immunoprecipitation (IP) and then analysed by Western blotting (WB). This analysis revealed that human tau directly interacts with the ΔSil1 and Δ Sil1Δ constructs, and also BiP (see FIG. 1). The majority of Tau protein in a cell resides in the cytoplasm whereas the majority of Sil1 is present in the ER as a result of the ER targeting signal and the ER retention sequence. However, when the ER targeting signal and the ER retention sequence are removed the majority of Sil1 localises to the cytoplasm thereby allowing an interaction with Tau to be detected. It should be understood that under normal physiological conditions (ie. expression of wild-type Tau and Sil1), only small amounts of each protein are likely to reside in the same compartment, hence the intrinsic detection limits of the methods, immunoprecipitation and immunofluorescence, make it difficult to detect the interaction.

Example 2

Figure 2:
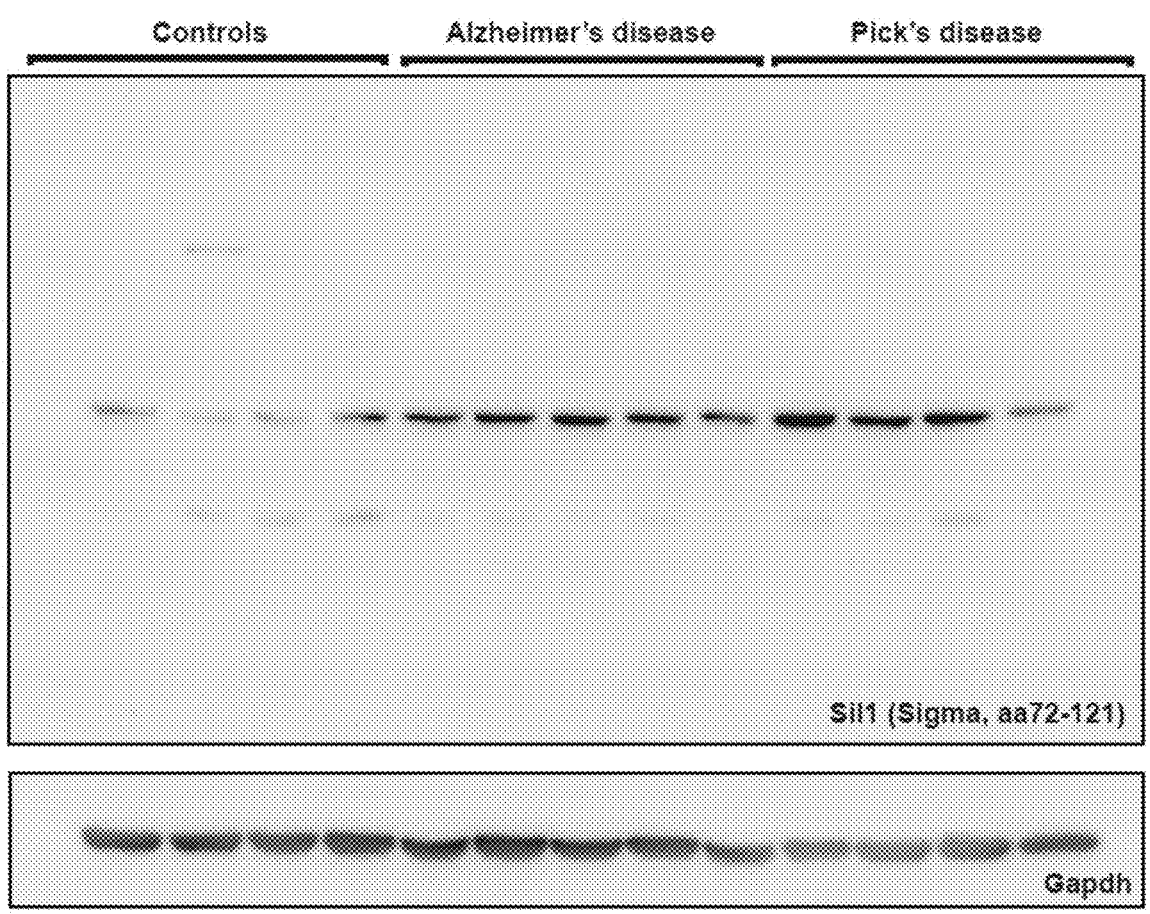
FIG. 2: Protein levels of Sil1 in samples from patient suffering Alzheimer's disease and Pick's disease were determined by Western blotting using Sil1-specific antibodies. Analysis with this antibody (from Sigma, targeting the starting region of the protein) suggests that protein levels of Sil1 are increased in Alzheimer's disease, and even more so in Pick's disease, compared to age-matched controls. Protein levels of the housekeeping protein Gapdh are shown for loading control.
Figure 3A:
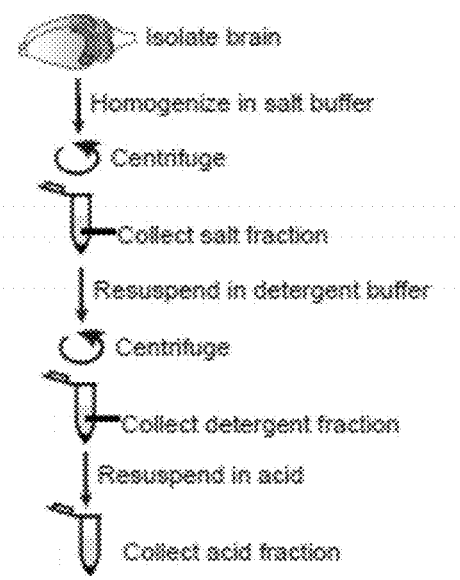
FIG. 3A: To assess the role of Sil1 in the development of tau pathology in vivo, we crossed Sil1 knockout mice (Sil1−/−) that carry a mutation in the Sil1 gene that results in lack of the Sil1 protein, with mice that overexpress P301L mutant human tau (pR5), causing them to develop tau pathology. Proteins were extracted from mouse brain tissue based on their solubility in buffers of increasing stringency, using a well-established protocol (see diagram).
Figure 3B:
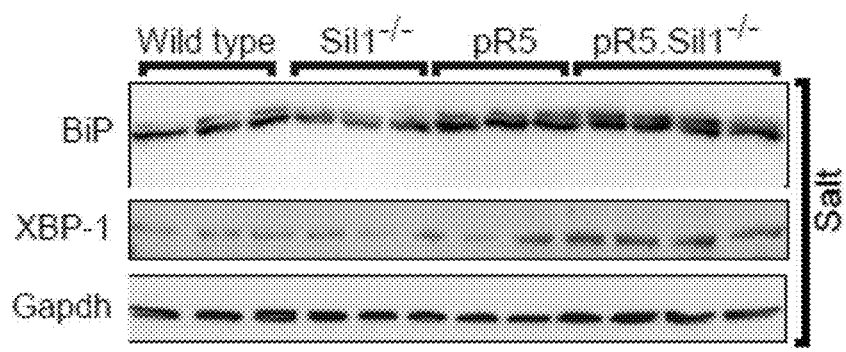
FIG. 3B Proteins in the salt buffer fraction were then analysed by Western blotting to assess the extent of ER stress occurring in these animals.
Figure 3C:
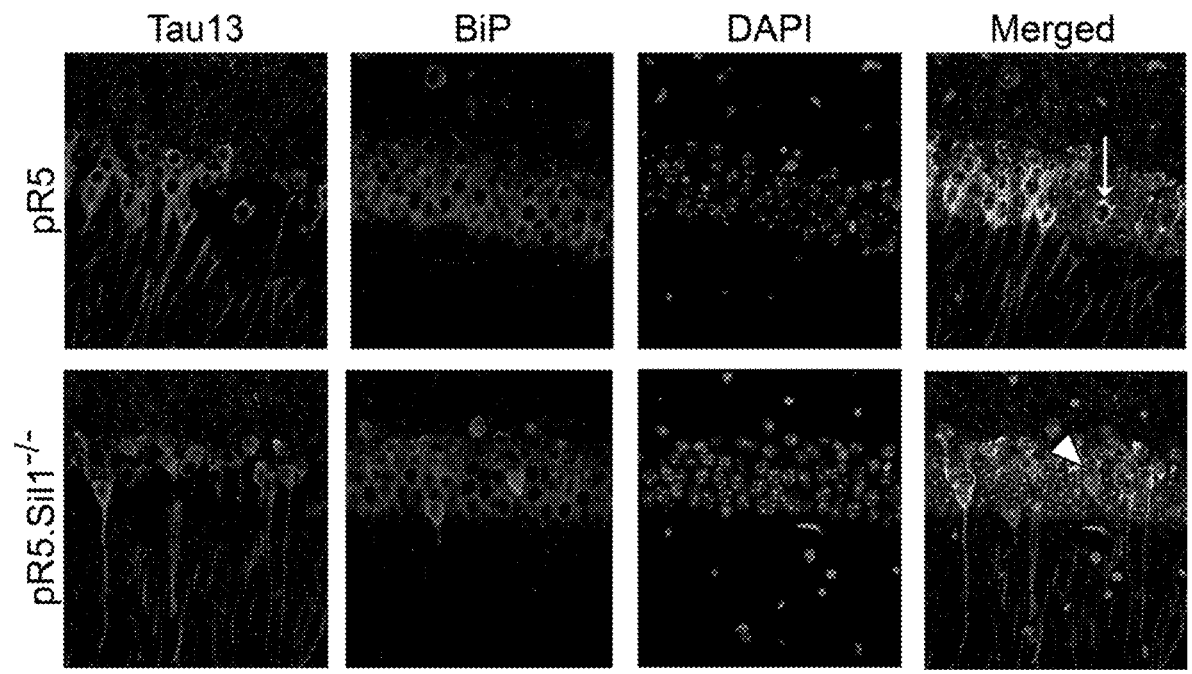
FIG. 3C Brain sections from these mice were also analysed with immunocytochemistry to determine the expression patterns of tau and BiP. Examination of the hippocampus revealed an abundance of tau (Tau13) and BiP in this area. Furthermore, the expression pattern of these two proteins was found to overlap to a large extent (as indicated by the arrow). We also observed that in cells that were highly positive for BIP (indicated by arrow head) the detection of tau was much lower.
Figure 3D:
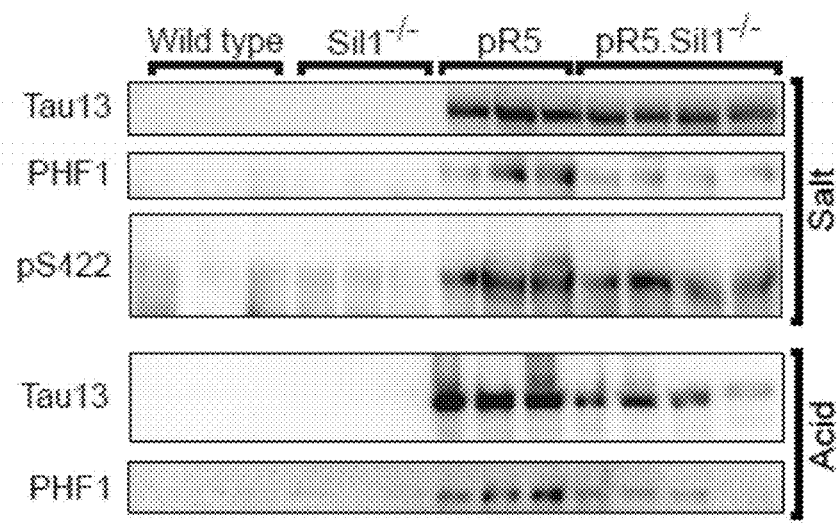
FIG. 3D The tau pathology was assessed in these mice by analysing tau solubility and phosphorylation with Western blotting. Total tau levels (Tau13) were similar in pR5 and pR5.Sil1−/− mice in the salt buffer fraction. However, there were significantly higher levels of phosphorylated tau (detected by PHF1 and pS422) in the pR5 mice compared to the pR5.Sil1−/− mice. The acid fraction from these mice was also analysed, which contains pathologically insoluble proteins. This revealed that pR5 mice develop abundant amounts of pathologically insoluble tau (Tau13), however in pR5.Sil1−/− mice these levels are dramatically reduced. Furthermore, whereas the pathologically insoluble tau is strongly phosphorylated (PHF1) in the pR5 mice, the pR5.Sil1−/− mice show virtually no phosphorylation.

Alzheimer's disease and Pick's disease are two common causes of dementia that are both neuropathologically characterised by abnormal tau pathology. We analysed protein levels of Sil1 in both of these disorders by Western blotting using Sil1-specific antibodies. Analysis with this antibody (from Sigma, targeting the starting region of the protein) suggests that protein levels of Sil1 are increased in Alzheimer's disease, and even more so in Pick's disease, compared to age-matched controls. Protein levels of the housekeeping protein Gapdh are shown for loading control. (see FIG. 2)

Example 3

To assess the role of Sil1 in the development of tau pathology in vivo, we crossed Sil1 knockout mice (Sil1−/−) that lack the Sil1 protein, with mice that overexpress mutant human tau (pR5), causing them to develop tau pathology.

Proteins were extracted from mouse brain tissue based on their solubility in buffers of increasing stringency, using a well-established protocol (see diagram). Proteins in the salt buffer fraction were then analysed by Western blotting to assess the extent of ER stress occurring in these animals. Protein levels of both BIP and spliced XBP-1 were increased in the pR5.Sil1−/− mice compared to the wild type mice, indicating moderate levels of ER stress in these mice.

Brain sections from these mice were also analysed with immunocytochemistry to determine the expression patterns of tau and BiP. Examination of the hippocampus revealed an abundance of tau (Tau13, shown in red) and BiP (shown in green) in this area. Furthermore, the expression pattern of these two proteins was found to overlap to a large extent (as indicated by the arrow). We also observed that in cells that were highly positive for BIP (indicated by arrow head) the detection of tau was much lower.

We then assessed the tau pathology in these mice by analysing tau solubility and phosphorylation with Western blotting. Total tau levels (Tau13) were similar in pR5 and pR5.Sil1−/− mice in the salt buffer fraction. However, there were significantly higher levels of phosphorylated tau (detected by PHF1 and pS422) in the pR5 mice compared to the pR5.Sil1−/− mice. This therefore, suggests that loss of Sil1 can reduce pathological phosphorylation of tau. We also analysed the acid fraction from these mice, which contains pathologically insoluble proteins. This revealed that pR5 mice develop abundant amounts of pathologically insoluble tau (Tau13), however in pR5.Sil1−/− mice these levels are dramatically reduced. Furthermore, whereas the pathologically insoluble tau is strongly phosphorylated (PHF1) in the pR5 mice, the pR5.Sil1−/− mice show virtually no phosphorylation. This therefore suggests that loss of Sil1 reduces the development of pathologically insoluble and phosphorylated tau. (see FIG. 3).

Example 4

To assess the role of Sil1 in the development of tau pathology in vivo, we crossed Sil1 knockout mice (Sil1−/−)

that lack the Sil1 protein, with mice that overexpress mutant human tau (K3), causing them to develop tau pathology.

Using the same protocol as in FIG. 3, proteins were extracted from aged (14 month) mouse cortical brain tissue based on their solubility in buffers of increasing stringency. We then assessed the tau pathology in these mice, by analysing tau cleavage and phosphorylation with Western blotting. To do so, we utilised 4 different tau antibodies, each of which targets a different region of the tau protein. Analysis with these antibodies revealed that total levels of tau (Tau13, Tau5, HT7, Tau46) tend to be reduced in K3.Sil1+/− mice, and even more so in K3.Sil1−/− mice. Furthermore, the analysis reveals an increase in smaller tau fragments in the K3.Sil1+/− and K3.Sil1−/− mice, indicating an increase in tau cleavage in these mice. This therefore suggests that a loss of Sil1 increases tau cleavage, and possibly thereby tau clearance. Further analysis also demonstrated that the K3.Sil1+/− and K3.Sil1−/− mice display reduced levels of phosphorylated tau (pS422 and PHF-1) compared to K3 controls. This therefore suggests that loss of Sil1 also reduces tau phosphorylation in these mice.

By 4 weeks of age, K3 mice develop a strong motor impairment characterised by a tremor, hind limb clenching and postural instability. The severeness of the motor impairment can be assessed using the Rota Rod, where mice are placed on a rotating rod and the longest time each mouse can remain on the rotating rod is recorded. This analysis demonstrates that in the first week of testing, when the mice are 4 weeks of age, male K3.Sil1+/− and K3.Sil1−/− mice perform better on the Rota Rod compared to their K3 control littermates. No significant differences are observed in the female mice. This indicates that loss of Sil1 can slightly improve motor impairments early but not later on in K3 mice, probably due to the early developmental damages in K3 mice.

Figure 4A:
FIG. 4A: To assess the role of Sil1 in the development of tau pathology in vivo, we crossed Sil1 knockout mice (Sil1−/−) that lack the Sil1 protein, with mice that overexpress mutant human tau (K3), causing them to develop tau pathology. Using the same protocol as in FIG. 3, proteins, were extracted from aged (14 month) mouse cortical brain tissue based on their solubility in buffers of increasing stringency.
Figure 4B:
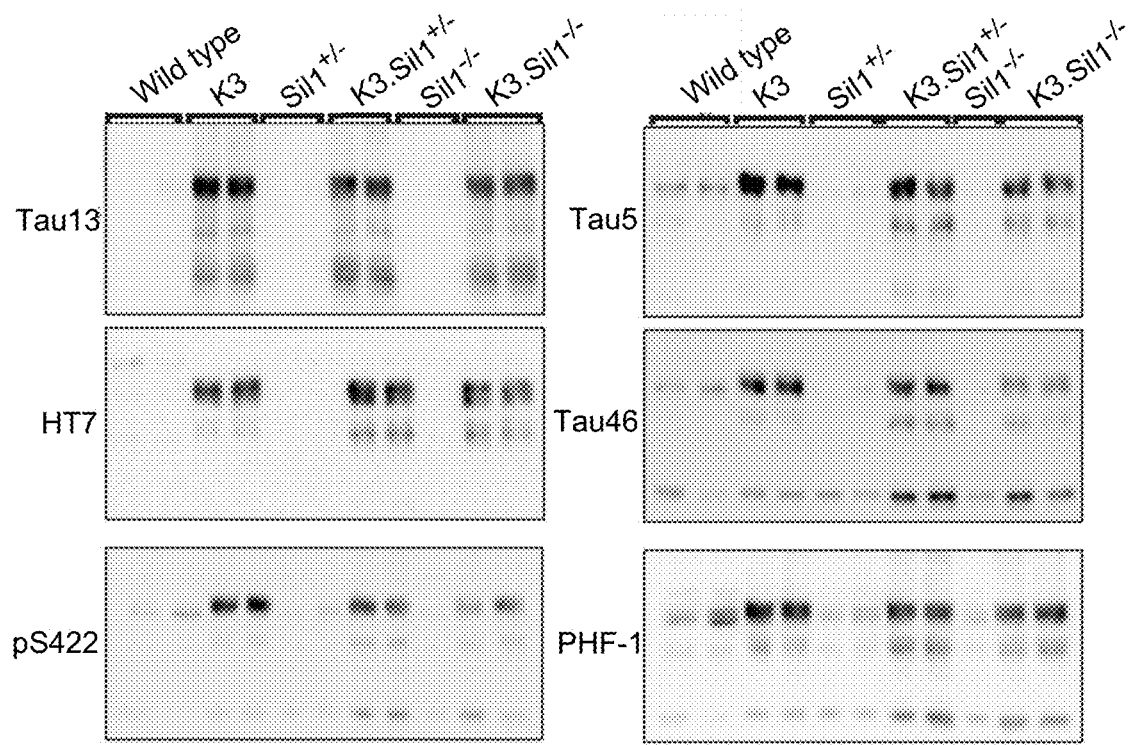
FIG. 4B: The tau pathology in these mice was assessed by analysing tau cleavage and phosphorylation with Western blotting. To do so, we utilised 4 different tau antibodies, each of which targets a different region of the tau protein. Analysis with these antibodies revealed that total levels of tau (Tau13, Tau5, H17, Tau46) tend to be reduced in K3.Sil1+/− mice, and even more so in K3.Sil1−/− mice. Furthermore, the analysis reveals an increase in smaller tau fragments in the K3.Sil1+/− and K3.Sil1−/− mice, indicating an increase in tau cleavage in these mice. Further analysis also demonstrated that the K3.Sil1+/− and K3.Sil1−/− mice display reduced levels of phosphorylated tau (pS422 and PHF-1) compared to K3 controls.
Figure 9:
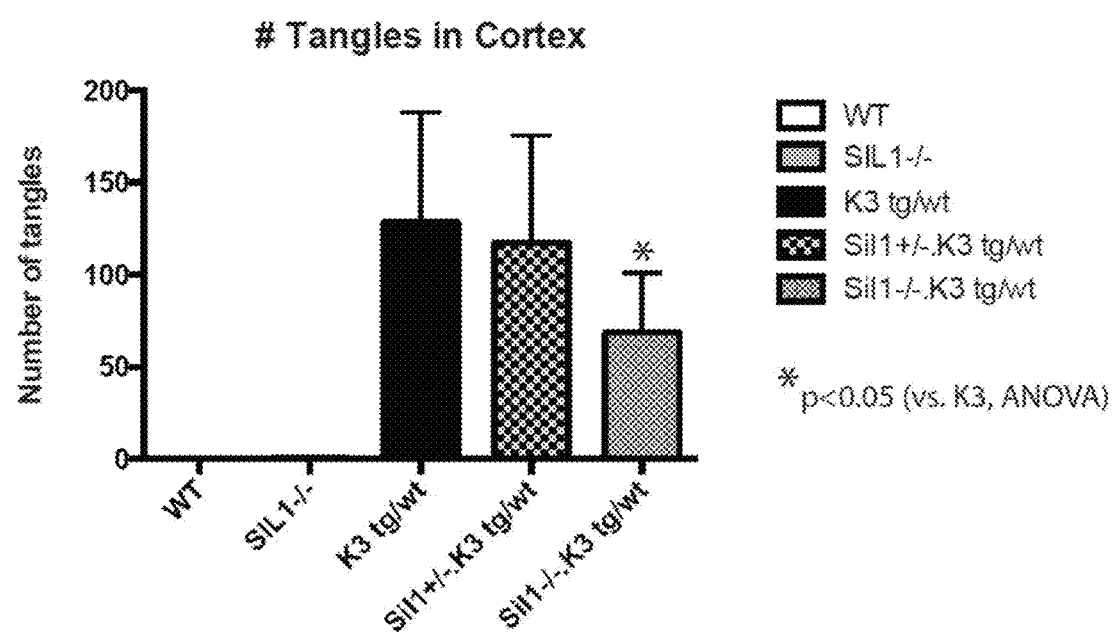
FIG. 9: Depletion of Sil1 reduces the formation of tau tangles within the cortex of aged K369I mutant tau transgenic mice. Brain sections from 10 months old K3 mice crossed with Sil1 knockout mice were stained with Bielschowsky silver to detect neuro-brillary tangles (NFTs). The number of Bielschowsky-silver positive NFT-like lesions within the cortex are slightly reduced in Sil1+/−.K3 mice and significantly reduced in Sil1−/−.K3 mice.

Brain slices from these mice were also analysed using silver staining to detect the bundled axons of cerebellar basket cells that form Pinceau terminals (arrow) around Purkinje cells. Aged K3 mice show a pronounced degeneration of Pinceau terminals, as demonstrated by the lack of silver-positive axons (arrow head) compared to both wild type controls and Sil1−/− mice. However, there is only a minor reduction of Pinceau terminals in K3.Sil1+/− mice, and normal numbers of Pinceau terminals in K3.Sil1−/− mice, compared to controls. This therefore suggests that loss of Sil1 can prevent neuronal loss and degeneration. (see FIG. 4)

Example 5

Depletion of Sil1 reduces the formation of tau tangles within the cortex of aged K369I mutant tau transgenic mice. Brain sections from 10 months old K3 mice crossed with Sil1 knockout mice were stained with Bielschowsky silver to detect neurobrillary tangles (NFTs). The number of Bielschowsky-silver positive NFT-like lesions within the cortex are slightly reduced in Sil1+/−.K3 mice and significantly reduced in Sil1−/−.K3 mice. There is an approximately 40% reduction in the number of tangles in the K3 mice with a homozygous knockout of Sil1 genes. Neurobrillary tangles are the ultimate readout that correlate with long term human tauopathies, in particular Alzheimer's disease.

Example 6

The following example describes a method to identify inhibitors of a protein-protein interaction of any two or more of the proteins described herein. The effectiveness of the invention could be demonstrated by the experiments described below.

Surface plasmon resonance (SPR) is a technique that allows the interaction between proteins to be analysed. SPR can be scaled up to a high-throughput format, such as in a protein array, to allow screening of multiple compounds for a capacity to inhibit a protein-protein interaction. A preferred SPR imaging system is one which has been developed to detect protein-ligand interactions in an array format on the surface of 2-D gold thin film (Jung et al. (2005) Proteomics, 5, 4427-4431).

Plasmid vectors for the recombinant expression of Sil1 and Tau could be prepared allowing production as fusion proteins with an affinity tag. An affinity tag is not required for SPR and is optional to assist in purification of the relevant protein. An example of a suitable fusion protein is, the nucleotide sequence of the longest human Tau isoform, htau40 (441 aa), or any other Tau isoform or fragment described herein, cloned into an expression vector that allows expression of a protein as a fusion with a glutathione S-transferase (GST) tag. Other suitable affinity tags include hexahistidine ($His_6$) and maltose binding protein (MBP). Further, the whole Sil1 protein or a fragment consisting of amino acids 31 to 449 of human Sil1 (SEQ ID NO: 2) could also be prepared as a fusion with a tag such as a $His_6$ tag. Preferably, the amino acid sequence of the Sil1 protein includes, consists essentially of or consists of any amino acid sequence that mediates binding to Tau with a similar affinity to amino acids 31 to 449 of human Sil1 (SEQ ID NO: 2).

The GST tagged Tau fusion can be purified from a 10 mL cell lysate by loading onto a GST-miniexcellose affinity column, washed with a PBS buffer to elute any unbound protein and eluted with 5 mL of 10 mM glutathione in PBS. The $His_6$-Sil1 fusion can be purified using a $Ni^{2+}$-IDS column.

The GST-Tau can be coupled to a gold chip using the following method. A clean gold chip is washed with ethanol containing 10 mM 11-mercapto-1-undecanol for about 16 hours. The hydroxyl group is activated using a 1:1 v/v ratio of 0.4M NaOH and 2-methoxyethyl ether containing 0.6M epichlorohydrin for 4 hours. A dextran of about 500,000 molecular weight can then be added to the surface in a solution of 0.3 mg/ml containing 0.1M NaOH for 20 hours. The dextran coated surface is then activated with 0.4M NaOH and 2-methoxyethyl ether containing 0.6M epichlorohydrin. Glutathione can then be coated onto the activated surface by incubating a 100 mg/ml L-glutathione solution (in a buffer of potassium phosphate at pH 7.0) at 37° C. for 20 hours. The coated chip is then washed with 1 M ethanolamine-HCl at 37° C. for 3 to 4 hours.

GST-Tau protein samples can be prepared in 96, 384 or 1536 well plates and spotted onto the glutathione coated gold chip using a protein arrayer. The spotted chip is then incubated at 37° C. for about 30 minutes before washed repeatedly with a PBS tween buffer.

To identify compounds that inhibit the interaction between Sil1 and Tau, each test compound at a particular concentration, e.g. 100 µM, is mixed with 10 µM of $His_6$-Sil1 and spotted onto the GST-Tau coated gold chip surface. A negative control could be $His_6$-Sil1 without any test compound.

A reduction in the intensity of the SPR image in the presence of the test compound compared to the intensity of the SPR image in the absence of the test compound indicates that there is a reduction in the interaction between $His_6$-Sil1 and GST-Tau. This indicates that the test compound is a potential inhibitor of the protein-protein interaction between Sil1 and Tau.

The example here describes the screening of compounds for inhibitors of the Sil1/Tau interaction, however the method could also be used to screen for inhibitors of the BiP/Tau or BiP/Sil1 interaction or of the Sil1/Tau/BiP complex. Where test compounds of the interaction between Sil1 and BiP are to be identified the Sil1 tagged fusion protein includes, consists essentially of or consists of any amino acid sequence that mediates binding to BiP with a similar affinity to amino acids 113 to 421 of human Sil1 (SEQ ID NO: 2). Further, the BiP tagged fusion includes, consists essentially of or consists of any amino acid sequence that mediates binding to Sil1 with a similar affinity to amino acids 43-426 of human BiP (SEQ ID NO: 3).

An advantage of the method described herein is that the protein-protein interactions can be analysed in high-throughput format without the use of labels. Further, the ability of the test compound to interact directly with the protein coated on the gold chip surface, i.e. the GST-Tau in the current example, can be tested.

The invention claimed is:

1. A method for determining whether a compound is useful in reducing Sil1 expression or activity including the steps of:
    providing a test compound selected from the group consisting of a small molecule, a peptide, or a peptidomimetic;
    providing a system that allows Sil1 expression or activity to be measured;
    contacting the system with the compound in conditions for permitting the compound to modulate Sil1 expression or activity;
    detecting modulation of Sil1 expression or activity in vitro;
wherein a reduction in Sil1 expression or activity indicates that the compound is useful in reducing Sil1 expression or activity; and
wherein the Sil1 activity measured is the interaction between Sil1 and Tau.

2. A method according to claim 1, wherein the Sil1 activity measured is the interaction between Sil1, Tau and BiP.

3. A method according to claim 1, wherein the Sil1 activity measured is the ability of Sil1 to induce nucleotide exchange.

4. A method according to claim 1, wherein the Sil1 expression measured is protein or mRNA levels.

5. A method according to claim 1 wherein the system is in vivo.

6. A method according to claim 1, wherein the Sil1 is an amino acid sequence consisting of amino acids 31 to 449 of human Sil1 (SEQ ID NO: 2).

7. A method according to claim 1, wherein the Sil1 is an amino acid sequence consisting of amino acids 113 to 421 of human Sil1 (SEQ ID NO: 2).

8. A method according to claim 2, wherein the Tau protein is a human Tau isoform selected from the group consisting of 0N3R, 0N4R, 1N3R, 1N4R, 2N3R and 2N4R.

9. A method according to claim 1 wherein the system that allows Sil1 expression or activity to be measured is selected from the group consisting of affinity purification mass spectrometry, genetic test systems such as yeast two hybrid, mating based split ubiquitin system, split reporter system, fluorescence resonance energy transfer (FRET), bioluminescence resonance energy transfer (BRET), atomic force microscopy, plasmon resonance such as quantitative surface plasmon resonance, calorimetry, GST pull-down, co-immunoprecipitation and NMR, for determining whether Sil1 expression or activity is modulated.

10. A method according to claim 9, wherein the split reporter system is a GFP split reporter system.

11. A method according to claim 1, further including the step of determining whether the compound reduces neurofibrillary tangles (NFTs) in an animal model.

12. A method according to claim 1, wherein the compound is part of a chemical library.

13. A method according to claim 1, wherein the Sil1 or Tau protein is isolated, recombinant or purified.

* * * * *

SEQUENCE LISTING

```
<160> NUMBER OF SEQ ID NOS: 4

<210> SEQ ID NO 1
<211> LENGTH: 1383
<212> TYPE: DNA
<213> ORGANISM: Homo sapiens

<400> SEQUENCE: 1
atggctcccc agagcctgcc ttcatctagg atggctcctc tgggcatgct gcttgggctg      60
ctgatggccg cctgcttcac cttctgcctc agtcatcaga acctgaagga gtttgccctg     120
accaacccag agaagagcag caccaaagaa acagagagaa aagaaaccaa agccgaggag     180
gagctggatg ccgaagtcct ggaggtgttc cacccgacgc atgagtggca ggcccttcag     240
ccagggcagg ctgtccctgc aggatcccac gtacggctga atcttcagac tggggaaaga     300
gaggcaaaac tccaatatga ggacaagttc cgaaataatt tgaaaggcaa aaggctggat     360
atcaacacca acacctacac atctcaggat ctcaagagtc cactggcaaa attcaaggag     420
ggggcagaga tggagagttc aaaggaagac aaggcaaggc aggctgaggt aaagcggctc     480
ttccgcccca ttgaggaact gaagaaagac tttgatgagc tgaatgttgt cattgagact     540
gacatgcaga tcatggtacg gctgatcaac aagttcaata gttccagctc cagtttggaa     600
gagaagattg ctgcgctctt tgatcttgaa tattatgtcc atcagatgga caatgcgcag     660
gacctgcttt cctttggtgg tcttcaagtg gtgatcaatg gctgaacag cacagagccc     720 ctcgtgaagg agtatgctgc gtttgtgctg ggcgctgcct tttccagcaa ccccaaggtc     780
caggtggagg ccatcgaagg gggagccctg cagaagctgc tggtcatcct ggccacggag     840
cagccgctca ctgcaaagaa gaaggtcctg tttgcactgt gctccctgct gcgccacttc     900
ccctatgccc agcggcagtt cctgaagctc gggggggctgc aggtcctgag gaccctggtg     960
caggagaagg gcacggaggt gctcgccgtg cgcgtggtca cactgctcta cgacctggtc    1020
acggagaaga tgttcgccga ggaggaggct gagctgaccc aggagatgtc cccagagaag    1080
ctgcagcagt atcgccaggt acacctcctg ccaggcctgt gggaacaggg ctggtgcgag    1140
atcacggccc acctcctggc gctgcccgag catgatgccc gtgagaaggt gctgcagaca    1200
ctgggcgtcc tcctgaccac ctgccgggac cgctaccgtc aggaccccca gctcggcagg    1260
acactggcca gcctgcaggc tgagtaccag gtgctggcca gcctggagct gcaggatggt    1320
gaggacgagg gctacttcca ggagctgctg ggctctgtca acagcttgct gaaggagctg    1380
aga                                                                   1383

<210> SEQ ID NO 2
<211> LENGTH: 461
<212> TYPE: PRT
<213> ORGANISM: Homo sapiens
```

<400> SEQUENCE: 2

```
Met Ala Pro Gln Ser Leu Pro Ser Ser Arg Met Ala Pro Leu Gly Met
1               5                   10                  15

Leu Leu Gly Leu Leu Met Ala Ala Cys Phe Thr Phe Cys Leu Ser His
            20                  25                  30

Gln Asn Leu Lys Glu Phe Ala Leu Thr Asn Pro Glu Lys Ser Ser Thr
        35                  40                  45

Lys Glu Thr Glu Arg Lys Glu Thr Lys Ala Glu Glu Leu Asp Ala
    50                  55                  60

Glu Val Leu Glu Val Phe His Pro Thr His Glu Trp Gln Ala Leu Gln
65              70                  75                  80

Pro Gly Gln Ala Val Pro Ala Gly Ser His Val Arg Leu Asn Leu Gln
                85                  90                  95

Thr Gly Glu Arg Glu Ala Lys Leu Gln Tyr Glu Asp Lys Phe Arg Asn
            100                 105                 110

Asn Leu Lys Gly Lys Arg Leu Asp Ile Asn Thr Asn Thr Tyr Thr Ser
        115                 120                 125

Gln Asp Leu Lys Ser Ala Leu Ala Lys Phe Lys Glu Gly Ala Glu Met
    130                 135                 140

Glu Ser Ser Lys Glu Asp Lys Ala Arg Gln Ala Glu Val Lys Arg Leu
145                 150                 155                 160

Phe Arg Pro Ile Glu Glu Leu Lys Lys Asp Phe Asp Glu Leu Asn Val
                165                 170                 175

Val Ile Glu Thr Asp Met Gln Ile Met Val Arg Leu Ile Asn Lys Phe
            180                 185                 190

Asn Ser Ser Ser Ser Leu Glu Glu Lys Ile Ala Ala Leu Phe Asp
        195                 200                 205

Leu Glu Tyr Tyr Val His Gln Met Asp Asn Ala Gln Asp Leu Leu Ser
    210                 215                 220

Phe Gly Leu Gln Val Val Ile Asn Gly Leu Asn Ser Thr Glu Pro
225                 230                 235                 240

Leu Val Lys Glu Tyr Ala Ala Phe Val Leu Gly Ala Ala Phe Ser Ser
                245                 250                 255

Asn Pro Lys Val Gln Val Glu Ala Ile Glu Gly Gly Ala Leu Gln Lys
            260                 265                 270

Leu Leu Val Ile Leu Ala Thr Glu Gln Pro Leu Thr Ala Lys Lys Lys
        275                 280                 285

Val Leu Phe Ala Leu Cys Ser Leu Leu Arg His Phe Pro Tyr Ala Gln
    290                 295                 300

Arg Gln Phe Leu Lys Leu Gly Gly Leu Gln Val Leu Arg Thr Leu Val
305                 310                 315                 320

Gln Glu Lys Gly Thr Glu Val Leu Ala Val Arg Val Val Thr Leu Leu
                325                 330                 335

Tyr Asp Leu Val Thr Glu Lys Met Phe Ala Glu Glu Ala Glu Leu
            340                 345                 350

Thr Gln Glu Met Ser Pro Glu Lys Leu Gln Gln Tyr Arg Gln Val His
        355                 360                 365

Leu Leu Pro Gly Leu Trp Glu Gln Gly Trp Cys Glu Ile Thr Ala His
    370                 375                 380

Leu Leu Ala Leu Pro Glu His Asp Ala Arg Glu Lys Val Leu Gln Thr
385                 390                 395                 400

Leu Gly Val Leu Leu Thr Thr Cys Arg Asp Arg Tyr Arg Gln Asp Pro
                405                 410                 415
```

Gln Leu Gly Arg Thr Leu Ala Ser Leu Gln Ala Glu Tyr Gln Val Leu
                420                 425                 430

Ala Ser Leu Glu Leu Gln Asp Gly Glu Asp Gly Tyr Phe Gln Glu
            435                 440                 445

Leu Leu Gly Ser Val Asn Ser Leu Leu Lys Glu Leu Arg
450                 455                 460

<210> SEQ ID NO 3
<211> LENGTH: 654
<212> TYPE: PRT
<213> ORGANISM: Homo sapiens

<400> SEQUENCE: 3

Met Lys Leu Ser Leu Val Ala Ala Met Leu Leu Leu Ser Ala Ala
1               5                   10                  15

Arg Ala Glu Glu Glu Asp Lys Lys Glu Asp Val Gly Thr Val Val Gly
            20                  25                  30

Ile Asp Leu Gly Thr Thr Tyr Ser Cys Val Gly Val Phe Lys Asn Gly
            35                  40                  45

Arg Val Glu Ile Ile Ala Asn Asp Gln Gly Asn Arg Ile Thr Pro Ser
50                  55                  60

Tyr Val Ala Phe Thr Pro Glu Gly Arg Leu Ile Gly Asp Ala Ala
65                  70                  75                  80

Lys Asn Gln Leu Thr Ser Asn Pro Glu Asn Thr Val Phe Asp Ala Lys
                85                  90                  95

Arg Leu Ile Gly Arg Thr Trp Asn Asp Pro Ser Val Gln Gln Asp Ile
                100                 105                 110

Lys Phe Leu Pro Phe Lys Val Val Glu Lys Lys Thr Lys Pro Tyr Ile
            115                 120                 125

Gln Val Asp Ile Gly Gly Gly Gln Thr Lys Thr Phe Ala Pro Glu Glu
        130                 135                 140

Ile Ser Ala Met Val Leu Thr Lys Met Lys Glu Thr Ala Glu Ala Tyr
145                 150                 155                 160

Leu Gly Lys Lys Val Thr His Ala Val Val Thr Val Pro Ala Tyr Phe
                165                 170                 175

Asn Asp Ala Gln Arg Gln Ala Thr Lys Asp Ala Gly Thr Ile Ala Gly
            180                 185                 190

Leu Asn Val Met Arg Ile Ile Asn Glu Pro Thr Ala Ala Ala Ile Ala
        195                 200                 205

Tyr Gly Leu Asp Lys Arg Glu Gly Glu Lys Asn Ile Leu Val Phe Asp
210                 215                 220

Leu Gly Gly Gly Thr Phe Asp Val Ser Leu Leu Thr Ile Asp Asn Gly
225                 230                 235                 240

Val Phe Glu Val Val Ala Thr Asn Gly Asp Thr His Leu Gly Gly Glu
                245                 250                 255

Asp Phe Asp Gln Arg Val Met Glu His Phe Ile Lys Leu Tyr Lys Lys
            260                 265                 270

Lys Thr Gly Lys Asp Val Arg Lys Asp Asn Arg Ala Val Gln Lys Leu
        275                 280                 285

Arg Arg Glu Val Glu Lys Ala Lys Arg Ala Leu Ser Ser Gln His Gln
290                 295                 300

Ala Arg Ile Glu Ile Glu Ser Phe Tyr Glu Gly Glu Asp Phe Ser Glu
305                 310                 315                 320

Thr Leu Thr Arg Ala Lys Phe Glu Glu Leu Asn Met Asp Leu Phe Arg 325                 330                 335
Ser Thr Met Lys Pro Val Gln Lys Val Leu Glu Asp Ser Asp Leu Lys
            340                 345                 350

Lys Ser Asp Ile Asp Glu Ile Val Leu Val Gly Gly Ser Thr Arg Ile
        355                 360                 365

Pro Lys Ile Gln Gln Leu Val Lys Glu Phe Phe Asn Gly Lys Glu Pro
    370                 375                 380

Ser Arg Gly Ile Asn Pro Asp Glu Ala Val Ala Tyr Gly Ala Ala Val
385                 390                 395                 400

Gln Ala Gly Val Leu Ser Gly Asp Gln Asp Thr Gly Asp Leu Val Leu
                405                 410                 415

Leu Asp Val Cys Pro Leu Thr Leu Gly Ile Glu Thr Val Gly Gly Val
            420                 425                 430

Met Thr Lys Leu Ile Pro Arg Asn Thr Val Val Pro Thr Lys Lys Ser
        435                 440                 445

Gln Ile Phe Ser Thr Ala Ser Asp Asn Gln Pro Thr Val Thr Ile Lys
    450                 455                 460

Val Tyr Glu Gly Glu Arg Pro Leu Thr Lys Asp Asn His Leu Leu Gly
465                 470                 475                 480

Thr Phe Asp Leu Thr Gly Ile Pro Pro Ala Pro Arg Gly Val Pro Gln
                485                 490                 495

Ile Glu Val Thr Phe Glu Ile Asp Val Asn Gly Ile Leu Arg Val Thr
            500                 505                 510

Ala Glu Asp Lys Gly Thr Gly Asn Lys Asn Lys Ile Thr Ile Thr Asn
        515                 520                 525

Asp Gln Asn Arg Leu Thr Pro Glu Glu Ile Glu Arg Met Val Asn Asp
    530                 535                 540

Ala Glu Lys Phe Ala Glu Glu Asp Lys Lys Leu Lys Glu Arg Ile Asp
545                 550                 555                 560

Thr Arg Asn Glu Leu Glu Ser Tyr Ala Tyr Ser Leu Lys Asn Gln Ile
                565                 570                 575

Gly Asp Lys Glu Lys Leu Gly Gly Lys Leu Ser Ser Glu Asp Lys Glu
            580                 585                 590

Thr Met Glu Lys Ala Val Glu Glu Lys Ile Glu Trp Leu Glu Ser His
        595                 600                 605

Gln Asp Ala Asp Ile Glu Asp Phe Lys Ala Lys Lys Lys Glu Leu Glu
    610                 615                 620

Glu Ile Val Gln Pro Ile Ile Ser Lys Leu Tyr Gly Ser Ala Gly Pro
625                 630                 635                 640

Pro Pro Thr Gly Glu Glu Asp Thr Ala Glu Lys Asp Glu Leu
                645                 650

<210> SEQ ID NO 4
<211> LENGTH: 441
<212> TYPE: PRT
<213> ORGANISM: Homo sapiens

<400> SEQUENCE: 4

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

```
Gln Thr Pro Thr Glu Asp Ser Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Ala Gly Ile Gly Asp Thr Pro
            100                 105                 110

Ser Leu Glu Asp Glu Ala Ala Gly His Val Thr Gln Ala Arg Met Val
            115                 120                 125

Ser Lys Ser Lys Asp Gly Thr Gly Ser Asp Asp Lys Lys Ala Lys Gly
            130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
            195                 200                 205

Arg Ser Arg Thr Pro Ser Leu Pro Thr Pro Pro Thr Arg Glu Pro Lys
210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
            275                 280                 285

Ser Lys Cys Gly Ser Lys Asp Asn Ile Lys His Val Pro Gly Gly Gly
            290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
            355                 360                 365

Lys Lys Ile Glu Thr His Lys Leu Thr Phe Arg Glu Asn Ala Lys Ala
370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
            435                 440
```